(12) United States Patent
Takahashi

(10) Patent No.: US 7,667,211 B2
(45) Date of Patent: Feb. 23, 2010

(54) ILLUMINATION LIGHT DETECTING OPTICAL SYSTEM AND OPTICAL APPARATUS AND ENDOSCOPE APPARATUS PROVIDED WITH THE SAME

(75) Inventor: Susumu Takahashi, Iruma (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/152,333

(22) Filed: May 13, 2008

(65) Prior Publication Data
US 2008/0283770 A1    Nov. 20, 2008

(30) Foreign Application Priority Data
May 15, 2007    (JP) .............................. 2007-129555

(51) Int. Cl.
    *F21V 9/16*    (2006.01)
(52) U.S. Cl. .................................................. 250/458.1
(58) Field of Classification Search ............... 250/458.1;
    600/60, 407–476, 310, 477; 356/342, 369,
    356/376, 364; 606/7; 385/117; 348/45,
    348/65, 72; D24/138; 427/2.12; 396/17;
    436/546, 172, 800
    See application file for complete search history.

(56) References Cited

U.S. PATENT DOCUMENTS 6,350,261 B1 *    2/2002    Domankevitz et al. ........ 606/17

FOREIGN PATENT DOCUMENTS

JP          2006-158716          6/2006

* cited by examiner

*Primary Examiner*—David P Porta
*Assistant Examiner*—Kiho Kim
(74) *Attorney, Agent, or Firm*—Kenyon & Kenyon LLP

(57) ABSTRACT

An illumination light detecting optical system includes an element emitting excitation light; an insertion part of a long-narrow-shape; a fluorescence luminescence component arranged near a top of the insertion part; an excitation light guiding element which leads the excitation light emitted from the light emitting element to the fluorescence luminescence component; and a light detecting element which detects return light which is a part of the illumination light. The optical system is also provided with a pillar-shaped transparent component for irradiating illumination light arranged coaxially at a forward position of the fluorescence luminescence component; an illuminating-light-extracting-element for extracting the illumination light from the pillar-shaped transparent component, out of the illumination light which enters into the inside of the pillar-shaped transparent component; and a deflecting element by which the extracted illumination light is directed toward the light detecting element.

21 Claims, 8 Drawing Sheets

ILLUMINATION LIGHT DETECTING OPTICAL SYSTEM AND OPTICAL APPARATUS AND ENDOSCOPE APPARATUS PROVIDED WITH THE SAME

This application claims benefits of Japanese Patent Application No. 2007-129555 filed in Japan on May 15, 2007, the contents of which are hereby incorporated by reference.

BACKGROUND OF THE INVENTION

1. Field of the Invention

The present invention relates to an illumination light detecting optical system and an optical apparatus and an endoscope apparatus provided with the same, for detecting abnormal illumination light in an illumination optical system in which for example, a fluorescence luminescence component is irradiated by LD light etc. as excitation light, and light which is mixed with the excitation light and fluorescence from the fluorescence luminescence component is used as illumination light.

2. Description of the Related Art

So far, an endoscope has been used for observation of a part which is difficult to observe from the outside in cases such as a medical treatment and/or diagnosis of inside of body of a patient in the field of medicine, an inspection of inside of a pore formed in a product in the field of industry, etc.

Generally, an endoscope has an image transmission optical system, an objective optical system, a relay lens (in case of a rigid endoscope) an image guide fiber (in case of a flexible endoscope) etc., in the inside of an insertion part at a top part having a cylindrical shape with small diameter. And, it is constituted so that light emanated from an observation object and passes through these optical systems may be observed as an observation image through an eyepiece optical system or an image pick-up optical system. In a video endoscope, it is constituted that imaging elements, such as an objective optical system and CCD, are built in at the top part.

In an endoscope, an illuminating means for illuminating an observation object by an objective optical system is arranged.

The illuminating means comprises a light source, a light guide which leads the illuminating light from the light source to a top part of the endoscope.

As the light source in a conventional endoscope apparatus, for illuminating the inside of the space of an object of examination brightly, lamps having comparatively large power consumption (a halogen lamp, a xenon lamp, a metal halide lamp) have generally been used. In recent years, in order to aim at reduction of power consumption, semiconductor light emitting element of low power (LED, LD) has been used as a light source.

For example, in an endoscope apparatus using LD for the light source, it is constituted such that excitation light of the predetermined wavelength emanated from LD is irradiated to a fluorescence luminescence component arranged in the top insertion part of the endoscope through a light guiding means which consists of optical fiber, etc., and in a fluorescence luminescence component, white color light converted by mixing excitation light and the excited fluorescence is irradiated to a space of an object to be examined (an examination object space).

By the way, in an endoscope, failure of light source (LD) and the like may happen, and an optical fiber of a light guiding means may be broken. In such state, if it continues using it as it is, light leaks out, and an amount of illumination light irradiated from the top of an insertion-part of the endoscope decreases, and accordingly an object to be examined (an examination object) will become dark. In a conventional endoscope, in order to control an electric power supply to a light source (LD) (for example, the electric power supply to the light source is stopped when an amount of light is small), a constitution equipped with an illumination light detecting means in which a predetermined amount of the illumination light is extracted, and its intensity is detected has been proposed.

The illumination light detecting means shown in Publication of the Japanese unexamined patent application, Toku Kai 2006-158716 is constituted as shown in FIGS. 1 and 2. For example, it is constituted so that light emitted from a side 151a (FIG. 1) of a fluorescence luminescence component 151 arranged to the a top part 150 of an endoscope, and an end surface 151b (FIG. 2) that is at the opposite side to an object to be examined (examination object) is received by light sensors 152 (FIG. 1) and 152 (FIG. 2).

In the FIGS. 1 and 2, a numerical symbol 153 is an illumination light source for lighting LD having a wavelength characteristics for exciting a fluorescence luminescence component 151, a numerical symbol 154 is a light guiding means which leads the light emanated from the illumination light source 153 to the fluorescence luminescence component 152, numerical symbols 155 and 155' are light guiding means in which light emanated from a side 151a (FIG. 1) of the fluorescence luminescence component 151, and an end face 151b (FIG. 2) that is at an opposite side of an examination object is led to light sensors 152 and 152', and a numerical symbol 156 is a communication line (illustration is not shown) for sending a signal of the light received by the light sensors 152, and 152 to the optical detecting means.

SUMMARY OF THE INVENTION

The illumination light detecting optical system according to the present invention is an optical system for detecting illumination light (illumination light detecting optical system) which is used for an optical apparatus, comprises a light emitting element which emits excitation light; an insertion part of a long-narrow-shape; a fluorescence luminescence component arranged near the top of the insertion part; an excitation light guiding means which leads the excitation light emitted from the light emitting element to the fluorescence luminescence component; and a light detecting means which detects return light which is a part of the illumination light, and it is characterized in that it comprises a first pillar-shaped transparent component for irradiating illumination light, which is arranged coaxially at a forward position of the fluorescence luminescence component; an illumination light-extracting means which extracts the illumination light which enters at an angle smaller than a total reflection angle to the side surface of the first pillar-shaped transparent component from the first pillar-shaped transparent component, out of illumination light which is emanated in a forward direction from the fluorescence luminescence component, and enters into the inside of the first pillar-shaped transparent component; and a deflecting means by which the extracted illumination light is directed toward the light detecting means.

Furthermore, in the illumination light detecting optical system according to the present invention, preferably, the total reflection angle is about 60 degrees.

Furthermore, in the illumination light detecting optical system according to the present invention, preferably it is constituted such that the illumination light extracting means consists of a transparent medium having a refractive index smaller than that of the first pillar-shaped transparent component and a joining function; and a second pillar-shaped transparent component for illumination light extraction that has the same refractive index of the first pillar-shaped transparent component, wherein the side surface of the second pillar-shaped transparent component is joined through the transparent medium to the side surface of the first pillar-shaped transparent component.

In the illumination light detecting optical system according to the present invention, preferably the transparent medium consists of adhesives and a ball lens.

In the illumination light detecting optical system according to the present invention, the illuminating light detecting optical system is used for an optical apparatus, and it comprises a light emitting element for emitting excitation light; an insertion part of a long-narrow-shape; a fluorescence luminescence component arranged near the top of the insertion part; an excitation light guiding means which leads the excitation light emitted from the light emitting element to the fluorescence luminescence component; and a light detecting means which detects return light which is a part of the illumination light; and preferably it has an illumination light extracting means which consists of the second pillar-shaped transparent component arranged so that the emitted light which is emanated from the very small part of the area out of illumination light emitted toward a forward direction from the fluorescence luminescence component, wherein a part of area of an entrance surface overlap with a very small part of area of an exit surface of the fluorescence luminescence component, may be extracted through a part of the area of the entrance surface; and a deflecting means by which the extracted illumination light is directed toward the light detecting means.

In the illumination light detecting optical system according to the present invention, preferably the deflecting means is constituted with a reflective surface consisting of a tilt surface formed at the top of the second pillar-shaped transparent component, and a reflective film arranged at the tilt surface.

In the illumination light detecting optical system according to the present invention, preferably the deflecting means is constituted with two reflective surfaces consisting of two tilt surfaces formed at the top of the second pillar-shaped transparent component, and a reflective film arranged at the two tilt surfaces.

Furthermore, the optical apparatus according to the present invention, is provided with one of optical systems for illumination light detection of the present invention mentioned above, a light emitting element which emits excitation light; an insertion part of a long-narrow-shape; a fluorescence luminescence component arranged near the top of the insertion part; an excitation light guiding means which leads the excitation light emitted from the light emitting element to the fluorescence luminescence component; and a light detecting means for detecting return light which is a part of the illumination light.

The optical apparatus according to the present invention is provided with one of illumination light detecting optical systems of the present invention mentioned above; a light emitting element which emits excitation light; an insertion part of a long-narrow-shape; a fluorescence luminescence component arranged near the top of the insertion part; an excitation light guiding means which leads the excitation light emitted from the light emitting element to the fluorescence luminescence component; a light detecting means for detecting return light which is a part of the illumination light; and the first pillar-shaped transparent component which is arranged at a forward position of the fluorescence luminescence component.

In the optical apparatus according to the present invention, preferably the light detecting means is provided with a spectrum component which separates the light obtained through the illumination light detecting optical system into an excitation light component and a fluorescence component; light receiving elements which receive each of separated light; an arithmetic apparatus for computing ratio of amounts of light received by each of the light receiving elements.

In the optical apparatus according to the present invention, preferably it is provided with a light diffusing means at the top end surface of the first pillar-shaped transparent component.

In the optical apparatus according to the present invention, preferably the light diffusing means is constituted such that a top end surface of the first pillar-shaped transparent component, and an end surface of a transparent component having the same refractive index as that of the first pillar-shaped transparent component are joined, wherein a ball lens array having different refractive index and adhesives are disposed between the surfaces.

In the optical apparatus according to the present invention, preferably the light diffusing means is constituted so that a sand pattern may be formed on, at least, one of the surfaces of the top end surface of the first pillar-shaped transparent component, and an end surface of a transparent component having the same refractive index as that of the first pillar-shaped transparent component, and further these surfaces are joined so that adhesives having different refractive index is disposed between the surfaces.

In the optical apparatus according to the present invention, preferably the optical apparatus is an endoscope.

Furthermore, the optical apparatus according to the present invention, is characterized in that it is provided with a light emitting element which emits excitation light; an insertion part inserted into an examination space, a fluorescence luminescence component arranged near the top of the insertion part; a light detecting means for detecting return light which is a part of the illumination light; one of illumination light detecting optical systems of the present invention; a light guide for detecting light, which is arranged so that one end may be faced to a rear end of the second pillar-shaped transparent component of the illumination light detecting optical system, and the other end may be faced to the optical sensor, wherein a part of light emanated to a forward direction from the fluorescence luminescence component is transmitted to the light sensor; a wavelength restriction component which is arranged between the other end of the light guide for light detection and the light sensor, wherein at least one of transmitting and reflecting of the light is carried out by restricting a part of wavelength of the light, and the light after having been transmitted or having been reflected is detected by the light sensor; and a controlling part, wherein the intensity of the one part of the light detected in the light sensor is detected, and then control for detecting degradation of the fluorescence luminescence component is carried out According to the present invention, an illumination light detecting optical system in which light loss of the light which is emanated from a fluorescence luminescence component and used as an illumination light can be stopped as much as possible, and further, illumination light can be examined with high precision, and an optical apparatus and an endoscope apparatus using the illumination light detecting optical system can be obtained by a simple constitution.

These and other features and advantages of the present invention will become apparent from the following detailed description of the preferred embodiments when taken in conjunction with the accompanying drawings.

DETAILED DESCRIPTION OF THE PREFERRED EMBODIMENTS

First Implementation Mode

Figure 2:
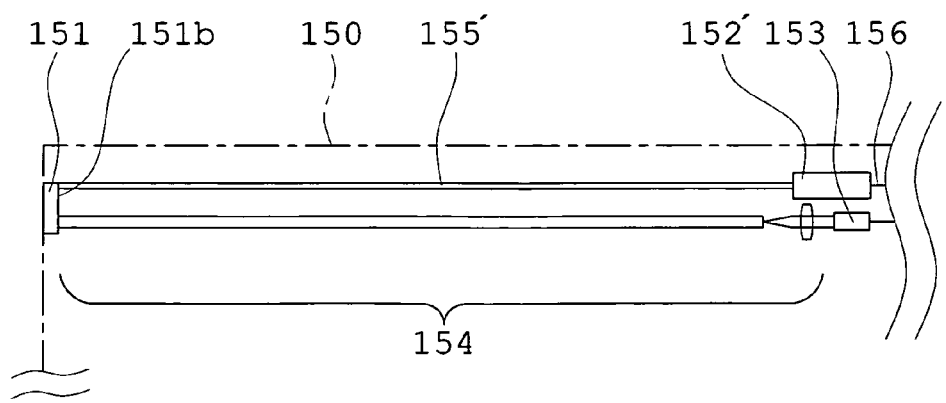
FIG. 2 is an explanatory diagram showing an outlined constitution of principal part of an illumination light detecting means regarding another conventional example.
Figure 3:
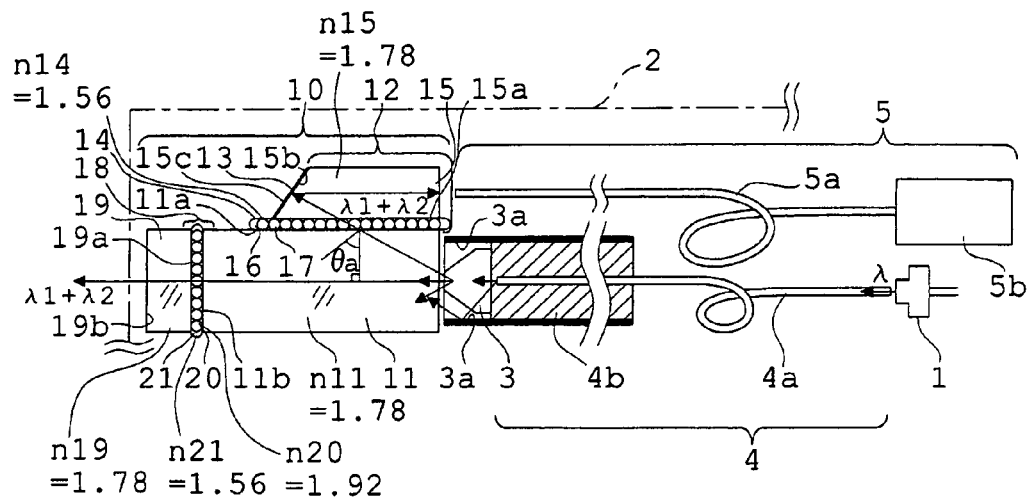
FIG. 3 is an explanatory diagram showing an outlined constitution of principal part of an optical device equipped with an illumination light detecting optical system of an embodiment 1 according to the present invention.
Figure 5:
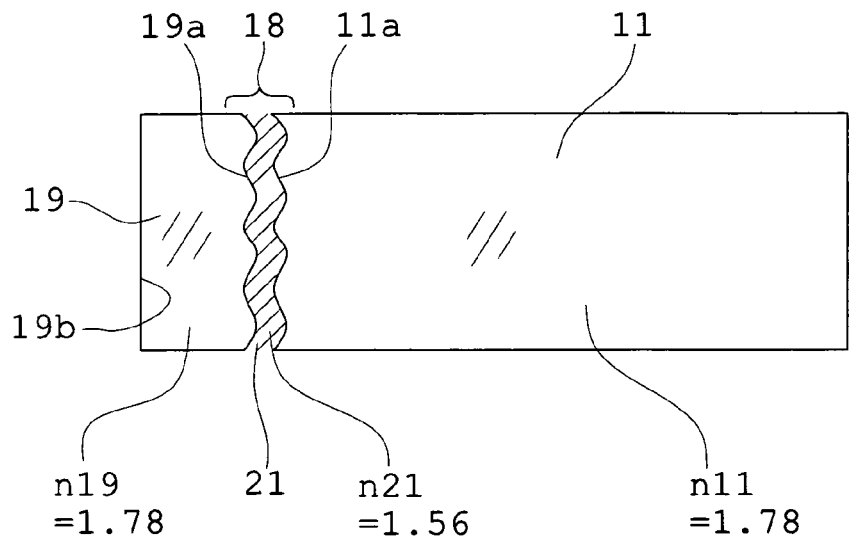
FIG. 5 is an explanatory diagram showing a modified example of light diffusion means arranged at a top part of the illumination light detecting optical system of the embodiment 1.

FIG. 3 is an explanatory diagram showing an outlined constitution of principal part of an optical apparatus equipped with an illumination light detecting optical system of the first embodiment according to the present invention. FIGS. 2A and 2B are explanatory diagrams showing constitutions of the principal part of the illumination light detecting optical system in the optical device of the first implementation mode, which is viewed from an object side. Here, an example and another example of constitution are shown, respectively. FIG. 5 is an explanatory diagram showing a modified example of light diffusing means arranged at a top part of the illumination light detecting optical system of the first implementation mode.

Figures 4A, 4B:
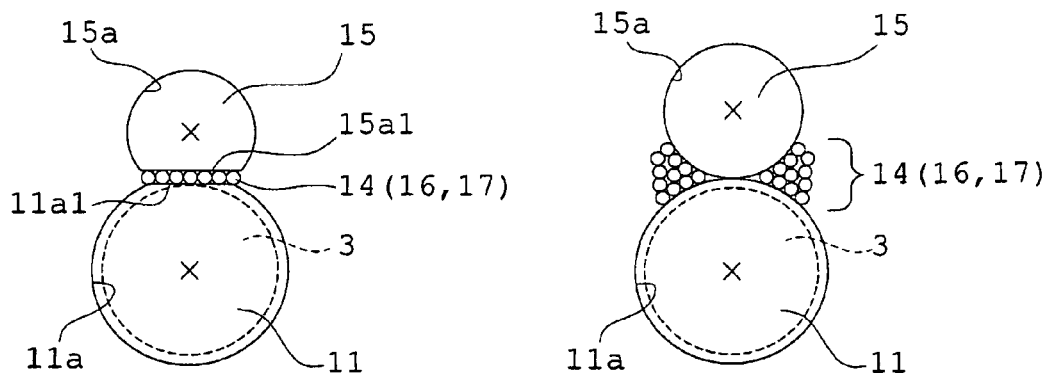
FIGS. 4A and 4B are explanatory diagrams showing constitutions of the principal part of the illumination light detecting optical system in the optical device of the first embodiment, which is viewed from an object. Here, an example and another example of constitution are shown, respectively.

The optical device of the first implementation mode comprises a light emitting element 1; an insertion part of a long-narrow-shape; a fluorescence luminescence component 3; an excitation light guiding means 4; a light detecting means 5 for detecting return light which is a part of the illumination light; and an illumination light detecting optical system. The light emitting element 1 is constituted so that excitation light of a wavelength of $\lambda 1$ may be emitted, using semiconductor light emitting element (LD) and the like, for example. The fluorescence luminescence component 3 is arrange 4 near the top of the insertion part 2, and is constituted so that mixed light of excitation light and fluorescence of the wavelength of $\lambda 2$ excited by the excitation light may be emitted as an illumination light. Moreover, the perimeter of the fluorescence luminescence component 3 is equipped with a cylindrical component having a reflective surface 3a inside. Thus by such constitution, an exit end area of illumination light is narrowed to a predetermined range around the optical axis at forward position. The excitation light guiding means 4 is constituted so that the excitation light emitted from the light emitting element 1 may be led to the fluorescence luminescence component 3 using optical fiber such as a single fiber, and the like. In FIGS. 4a is fiber (core+clad) and 4b is a holding component.

The light detecting means 5 is constituted with an illumination-light-for-detection guiding means 5a, and a light detecting part 5b which consists of a light receiving element, a light intensity detecting element, etc. The light receiving element consists of a semiconductor light receiving element such as PD (photo-diode) etc., for example. Here, the light detecting means 5 is not limited within the constitution shown FIG. 1, and it may be constituted with, for example, the light emitting element; a signal line which transmits information received by the light receiving element; and a light intensity detecting element. The illumination-light-for-detection guiding means 5a is constituted using optical fibers (single fiber), for example, and it is arranged so that a part of illumination lights may be led to the light receiving element of the light detecting part 5b. The light detecting part 5b is constituted so that it may detect the intensity of the illumination light received through the light receiving element.

The illumination light detecting optical system 10 comprises a pillar-shaped transparent component 11 for irradiating light (hereafter, "the first pillar-shaped transparent component"), an illumination light extracting means 12, and a deflecting means 13. The first pillar-shaped transparent component 11 having a mirror surface is arranged coaxially at a forward position of the fluorescence luminescence component 3. The illumination light-extracting means 12 is constituted such that it may extract the illumination light which enters at a predetermined angle smaller than a total reflection angle θa to the side surface 11a of the first pillar-shaped transparent component, out of illumination light which is emanated in a forward direction from the fluorescence luminescence component 3, and enters into the inside of the first pillar-shaped transparent component 11, from the side surface 11a of the first pillar-shaped transparent component 11.

Here, a more detailed constitution of the illumination light extraction means 12 shown in FIG. 3 will be explained. The illumination light-extracting means 12 consists of a transparent medium 14 which has a joining function and a refractive index smaller than that of the first pillar-shaped transparent component 11, and a pillar-shaped transparent component 15 for illumination light extraction, which has the same refractive index of that of the first pillar-shaped transparent component 11, (hereafter the second pillar-shaped transparent component). Here, as shown in FIG. 4A, by the transparent medium 14, a flat bonded surface 15a1 formed on a side surface 15a of the second pillar-shaped transparent component 15 is joined to a flat bonded surface 11a1 formed on the side surface 11a of the first pillar-shaped transparent component 11. The transparent medium 14 consists of adhesives 16 and an array of ball lenses (a ball lens-array) 17. The ball lens array 17 is used in order that the transparent medium 14 may be made to have a designated thickness easily.

In the example of FIG. 3, a material having refractive-index n11=1.78 is used for the first pillar-shaped transparent component 11. And, a material having refractive-index n14=1.56 is used for the transparent medium 14 (adhesives 16 and ball lens-array 17). A material having refractive-index n15=1.78 is used for the second pillar-shaped transparent component 15. The deflecting means 13 is constituted such that by using a reflective surface on which a reflective film 15c on a tilt surface 15b formed at the top of the second pillar-shaped transparent component 15 is formed, and via the illumination light-extracting means 12, illumination light which is extracted and directed toward a forward direction may be reflected toward the light detecting means 5. Further, the optical apparatus of the first implementation mode is provided with a light diffusing means 18 in a top end surface 11b of the first pillar-shaped transparent component 11. The light diffusing means 18 is constituted such that the top end surface 11b of the first pillar-shaped transparent component 11, and the an end surface side 19a of the transparent component 19 (n19=1.78) with the same refractive index as the first pillar-shaped transparent component 11 are joined by sandwiching a ball lens-array 20 having a different refractive index (refractive-index n20=1.92) and an adhesives 21 (refractive-index n21=1.56).

Then, functions of the optical apparatus having the illumination light detecting optical system of the first mode of implementation, which is constituted as mentioned above will be explained. Excitation light emitted from the light emitting element passes through the excitation light guiding means 4, and excises the fluorescence luminescence component 3. By this way, it becomes mixed illumination light which is mixed by the fluorescence excited by the fluorescence luminescence component 3 and the excitation light, and then it is emanated from the front of the fluorescence luminescence component 3, and then it enters into the first pillar-shaped transparent component 11. At this time, in the optical device having the illumination light detecting optical system of the first implementation mode, as for the illumination light-extracting means 12, a difference of refraction index of the first pillar-shaped transparent component 11 and the transparent medium 14 is given. Therefore, light which enters into the transparent medium 14 with an angle larger than a critical angle (total reflection angle) out of light passing through the first pillar-shaped transparent component 11 is totally reflected on a border plane, and at the same time, a part of light which enters with an angle smaller than the critical angle, and light which goes forward without entering into the transparent medium 14 by being reflected by the border plane are directed together toward the top end surface 11b of the first pillar-shaped transparent component 11. Mean while, a remaining part of the light which entered with the angle smaller than the critical angle is refracted in a direction approaching the first pillar-shaped transparent component 11, and it enters into the inside of the transparent medium 14. Here, when a critical angle is set to θ, the following can be expressed;

$\sin\theta = n14/n11$

Figure 1:
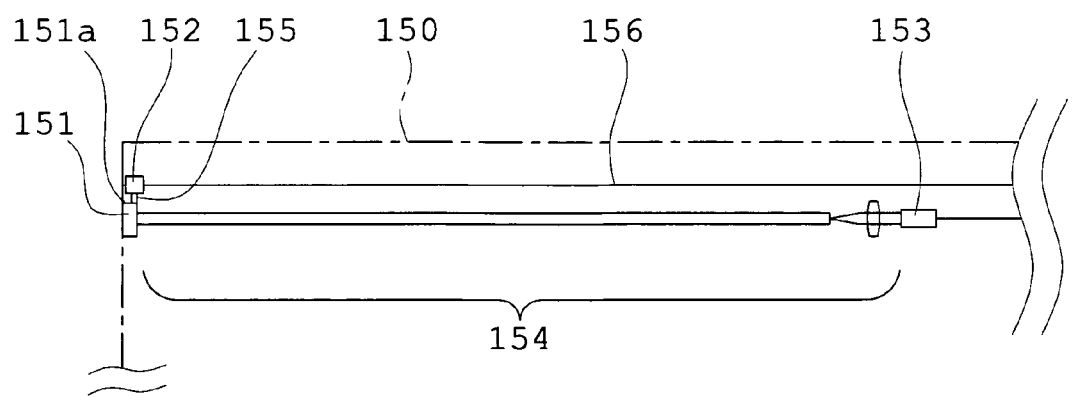
FIG. 1 is an explanatory diagram showing an outlined composition of principal part of an illumination light detecting means regarding one of conventional examples.

Therefore, the critical angle θa of the example in FIG. 1 can be expressed as follows.

$\sin\theta a = 1.56/1.78$ $\theta a \approx 60°$

Namely, in the example of FIG. 3, light entering into the transparent medium 14 at an angle smaller than about 60° from the first pillar-shaped transparent component 11 (namely, light which enters obliquely into the transparent medium 14 with an angle larger than about 30° to the optical axis of the first pillar-shaped transparent component 11) enters into the inside of the transparent medium 14, while being refracted in a direction approaching the first pillar-shaped transparent component 11. The light entering into the inside of the transparent medium 14, enters into the first pillar-shaped transparent component 11. At this time, since the refractive index of the second pillar-shaped transparent component 15 is larger than that of the transparent medium 14, a part of light is reflected by the transparent medium 14, and in meantime, the other remaining light enters into the inside of the second pillar-shaped transparent component 15, while being refracted in the direction to which it departs from the transparent medium 14. Light entering into the inside of the second pillar-shaped transparent component 15, is reflected by the deflecting means 13 and deflected to the side of the light-detection-means 5. Light deflected to the side of the light-detection-means 5 passes through the illumination-light-for-detection guiding means 5a, and it is received by the light detecting part 5b, wherein its intensity is detected.

In this way, in the illumination light detecting optical system of the first mode of implementation, the light entering obliquely into the transparent medium 14 with an angle larger than about 30° to the optical axis of the first pillar-shaped transparent component 11, out of the light which is emitted toward the forward direction of the fluorescence luminescence component 3, is used as light to be detected. However, light emanated from the front of the fluorescence luminescence component 3 at such an angle, in optical apparatus such as an endoscope, etc, is leaked-light which illuminates an area which is out of the observation angle of view of the objective optical system of which illustration is not shown, and accordingly, it is the light which is not used for observation. Therefore, according to the illumination light detecting optical system of the first embodiment, the light which is emitted toward the forward direction of the fluorescence luminescence component 3 is detected, and moreover, the leaked light illuminating the area which is not used for observation may be used as light to be detected. Therefore, while suppressing a light loss as much as possible, illumination light having the same ratio as that of the illumination light which illuminates an examination object as for a ratio of mixture of the fluorescence light and the excitation light can be detected with high precision.

Light directed toward the top end surface 11b of the first pillar-shaped transparent component 11 is emanated from the top end surface 11b, and when it passes through a ball lens array 20 (refractive-index n20=1.92) constituted as an light diffusing means 18, a adhesives 21 (refractive-index n21=1.56), and a transparent component 19 (n19=1.78) it is defused by a refraction action generated from each difference of refraction indexes, and through each of lens surfaces of the ball lens array 20. Thus, an amount of light of the illumination light in the exit surface 19b is equalized. According to the optical system of the present embodiment, illumination light of uniform brightness which excludes as much as possible unevenness in a bright and dark states of the illumination light for illuminating the examination object can be irradiated.

In the example of FIG. 4A, a flat bonded surface 15a1 formed on a side surface 15a of the second pillar-shaped transparent component 15 through the transparent medium 14 is joined to a flat bonded surface 11a1 formed on the side surface 11a of the first pillar-shaped transparent component 11. However, as shown in FIG. 4B, a predetermined area on the side surface 15a of the second pillar-shaped transparent component 15 may be joined through the transparent medium 14 to a predetermined area on the side surface 11a of the first pillar-shaped transparent component 11.

As shown in FIG. 4A, when flat joined surfaces are joined, a junction state of the first pillar-shaped transparent component 11 and the second pillar-shaped transparent component 15 is stabilized. As shown in FIG. 4B, when the predetermined area in the side surfaces are joined, a longer distance between the mutual optical axes of the first pillar-shaped transparent component 11 and the second pillar-shaped transparent component 15 can be obtained. Accordingly, it becomes easy to arrange the illumination-light-for-detection guiding means 5a for leading the illumination light emanated from the second pillar-shaped transparent component 15 to the light detecting part 5b.

In the example of FIG. 3, the deflecting means 13 is constituted with one reflective surface. However, it may be constituted such that two tilt surfaces are formed at the top of the second pillar-shaped transparent component 15, and two reflective surfaces (illustration is not shown) having reflective films on the two tilt surfaces are used, wherein illumination light which is extracted and directed toward forward direction may be reflected toward the light detecting means 5 via the illumination light-extracting means 12. Even if it does in this way, a longer distance between the mutual optical axes of the first pillar-shaped transparent component 11 and the second pillar-shaped transparent component 15 can be obtained, and it becomes easy to arrange the illumination-light-for-detection guiding means 5a for leading the illumination light emanated from the second pillar-shaped transparent component 15 to the light detecting part 5b.

As for the light diffusing means 18 having the top surface 11b of the first pillar-shaped transparent component 11, it may be constituted such that as shown in FIG. 5, a sand pattern is formed on, at least, one of the top end surface 11b of the first pillar-shaped transparent component 11, and the end surface side 19a of the transparent component 19 (n19=1.78) having the same refractive index as that of the first pillar-shaped transparent component 11, and these end surfaces (11b,19a) are joined so as to sandwich adhesives 21 having different refractive indexes. (refractive index n21=1.56). In the example of FIG. 5, the sand pattern is formed on both of end surfaces 11b and 19a. Even though it is constituted in this way, light directed toward the top end surface 11b of the first pillar-shaped transparent component 11 is diffused by refraction action which are generated from difference of refraction indexes, and through the surfaces 11b and 19a in which the sand pattern is formed. Thus, an amount of light of the illumination light in the exit surface 19b is equalized. Accordingly, illumination light of uniform brightness which excludes as much as possible unevenness in a bright and dark states of the illumination light for illuminating the examination object can be irradiated. Furthermore, the transparent component 19 may be constituted as a lens. For example, in the case that the examination object is observed with a wide angle, a large area can be illuminated if the top surface of the transparent component 19 is constituted as concave surface.

Figure 6:
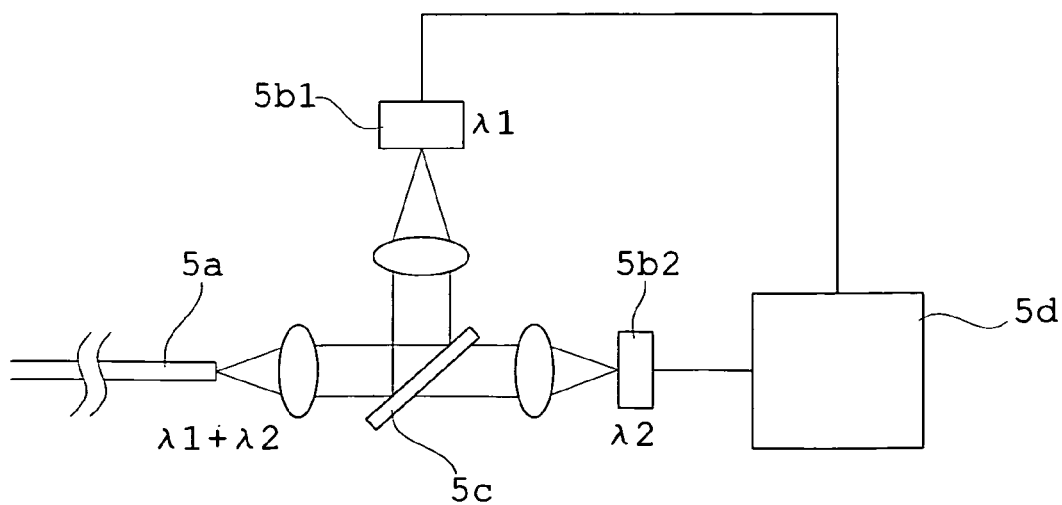
FIG. 6 is an explanatory diagram showing a modified embodiment of the light detecting means in the optical apparatus equipped with the illumination light detecting optical system of the first embodiment.

As shown in FIG. 6, more preferably the light detecting means 5 is constituted such that it is provided with a dichroic mirror 5c as a spectrum component for separating light obtained through the illumination light detecting optical system at the exit end side of the illumination-light-for-detection guiding means 5a into an excitation light component and a fluorescence component, and further it is provided with light receiving elements 5 b1 and 5 b2 on each of optical paths by which spectrum of the light is separated by the spectrum component, an arithmetic unit 5d which compute a ratio of an amount of the light which is received by each of the light receiving elements 5 b1 and 5b2. In the example of FIG. 6, the dichroic mirror 5c has characteristics that excitation light is reflected, and fluorescence may penetrate it. Furthermore, a dichroic mirror having characteristics that the excitation light is penetrated and the fluorescence is reflected may be used. In this way, by detecting change of color balance by detecting an amount of light for every wavelength degradation of a fluorescence luminescence component can be detected.

Second Implementation Mode

Figure 7:
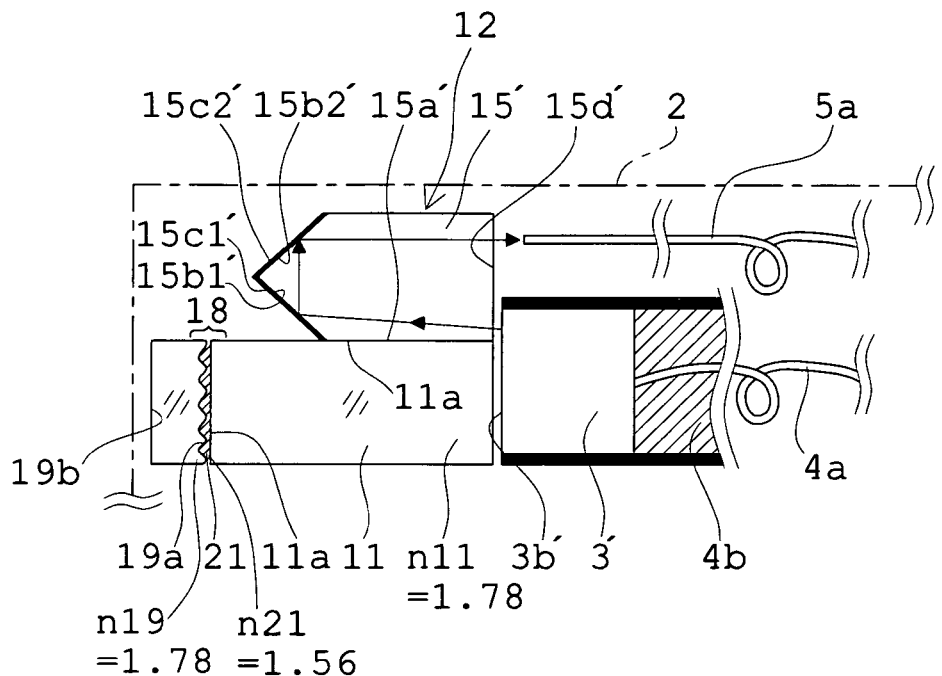
FIG. 7 is an explanatory diagram showing an outlined constitution of principal part of an optical apparatus equipped with an illumination light detecting optical system of a second embodiment according to the present invention.
Figure 8:
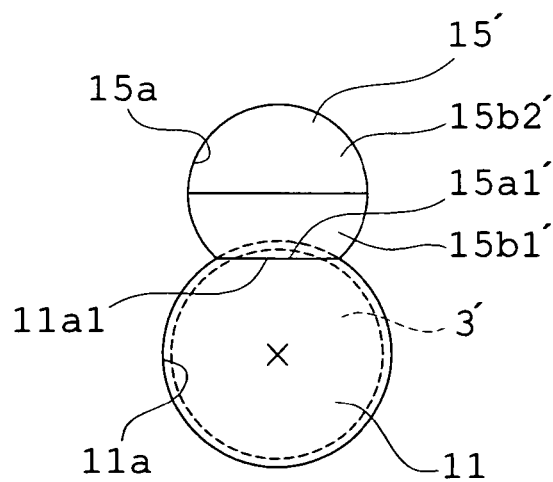
FIG. 8 is an explanatory diagram showing constitution of the principal part of the illumination light detecting optical system in the optical apparatus of the second embodiment, which is viewed from an object.

FIG. 7 is an explanatory diagram showing an outlined constitution of a principal part of an optical apparatus equipped with an illumination light detecting optical system of the second implementation mode according to the present invention. FIG. 8 is an explanatory diagram showing constitution of the principal part of the illumination light detecting optical system in the optical apparatus of the second mode of implementation, which is viewed from an object side.

In the optical device of the second mode of implementation, an illumination light extracting optical system 12 consists of only second pillar-shaped-transparent-component 15' for extracting illumination light. The second pillar-shaped transparent component 15' is constituted such that a part of area of an end surface 15d' overlaps with a very small part of area of an exit surface 3b' of the fluorescence luminescence component 3', and it is arranged such that light emanated from a very small part of the area, out of illumination light which is emanated toward the forward direction from the fluorescence luminescence component 3' may be extracted through the area of the end-faces' 15d. As for the fluorescence luminescence component 3', it differs from the fluorescence luminescence component 3 in the first embodiment, and it is constituted so that an illumination light may be emanated from whole area of the front side surface.

As shown in the FIG. 8, the second pillar-shaped-transparent-component 15' is constituted such that a flat bonded surface 15a1' formed on the side surface 15a' of the second pillar-shaped transparent component 15' is joined to a flat bonded surface 11a1 formed on the side surface 11a of the first pillar-shaped transparent component 11.

A deflecting means 13 is constituted such that two tilt surfaces 15b1', and 15b2' are formed at the top of the second pillar-shaped transparent component 15', and by using the two reflective surfaces (illustration is not shown) having reflective films 15c1', and 15c2' on the two tilt surfaces 15b1', and 15b2', illumination light which is extracted via the illumination light-extracting means 12, and directed toward forward direction may be reflected toward a light detecting means 5. On a side surface 11a of the first pillar-shaped transparent component 11, and a light shielding means (illustration is not shown) such as reflective film and the like which reflects the light towards the inside is arranged so that the illumination light may not enter into the inside of the second pillar-shaped-transparent-component 15' from the first pillar-shaped transparent component 11.

Besides this, a light diffusing means 18 is constituted such that a sand pattern is formed on an end surface side 19a of the transparent component 19 (n19=1.78) having the same refractive index as that of the first pillar-shaped transparent component 11, and the end surface 19a and the flat end surface 111b of the first pillar-shaped transparent component 11 are joined so as to sandwich adhesives 21 having different refractive index (refractive index n21=1.56). As for the other constitutions, it is almost the same to the optical apparatus equipped with the illumination light detecting optical system of the first mode of implementation.

Then, operations of the optical apparatus having the illumination light detecting optical system of the second mode of implementation, which is constituted as mentioned above will be explained. Excitation light emitted from the light emitting element (illustration is not shown) is transmitted through the excitation light guiding means 4, and by exciting a fluorescence luminescence component 3' it becomes illumination light which the fluorescence excited by the fluorescence luminescence component 3' and the excitation light are mixed, and then it is emanated from the front of the fluorescence luminescence component 3.

At this time, in the optical apparatus equipped with the illuminating light detecting the optical system of the second mode of implementation, the light emanated from area of a large portion of an exit surface 3b' which overlaps with the entrance surface of the first pillar-shaped transparent component 11 out of illuminating light which is emanated toward the forward direction from the fluorescence luminescence component 3', enters into the first pillar-shaped transparent component 11. Then, it is transmitted to a forward direction while reflecting, or without reflecting on the side surface 11a in which the reflective film is arranged at the inside, and then, it is directed toward the top end surface 11b of the first pillar-shaped transparent component 11. In meanwhile, light emanated from a very small part of the area of the exit surface 3b', which overlaps with a part of the area of end-face 15d' in the second pillar-shaped-transparent-component 15' enters into the inside of the second pillar-shaped-transparent-component 15' from the part of the area of the end-face 15d'. The light which has entered the inside of the second pillar-shaped transparent component 15, is reflected by two reflecting surfaces consisting of the deflecting means 13, and deflected to the side of the light-detection-means 5. The light deflected at the side of the light detecting means 5 passes through the illumination-light-for-detection guiding means 5a, and then, it enters into a light detecting part (illustration is not shown), and its intensity is detected.

In optical apparatus such as endoscope, some of them have a small exit angle of an illumination light. Even if a constitution which extracts leaked light having a larger angle than a total reflection angle as seen in the illumination light detecting optical system of the first implementation mode is applied to an optical apparatus with a narrow exit end angle of an illumination light, it is supposed that since leaked light is very little, sufficient amount of light for detection cannot be extracted. However, according to the optical apparatus equipped with the illumination light detecting optical system of the second mode of implementation, since the illumination light is extracted from a part of the area which overlap with the area of the exit surface 3b' of the fluorescence-luminescence-component 3' in the end surface 15' of the second pillar-shaped-transparent-component 15', a sufficient amount of light for detection can be extracted in an optical apparatus having a small exit end angle of illumination light. Moreover, since a part of light emitted toward a forward direction of the fluorescence-luminescence-component 3' is extracted via the first pillar-shaped-transparent-component 15', illumination light having the same ratio of mixture with excitation light to that of fluorescence can be detected with high precision.

Here, light directed toward the top end surface 11b of the first pillar-shaped transparent component 11 is emanated from the top end surface 11b, and when it is transmitted through the transparent component 19 (n19=1.78) which has adhesives 21 (refractive-index n=1.56) constituted as the optical diffusing means 18 and a transparent component 19 (n19=1.78) having an end face 19a on which a sand pattern is formed, it is diffused by an action of refraction generated from each of differences of refraction indexes, and through the surface 19a on which the sand pattern is formed. Thus, an amount of the illumination light in the exit surface 19b is equalized. As for the other functions, actions, and effects, these are almost the same to an optical apparatus equipped with the illumination light detecting optical system of the first mode of implementation.

Embodiment 1

Figure 9:
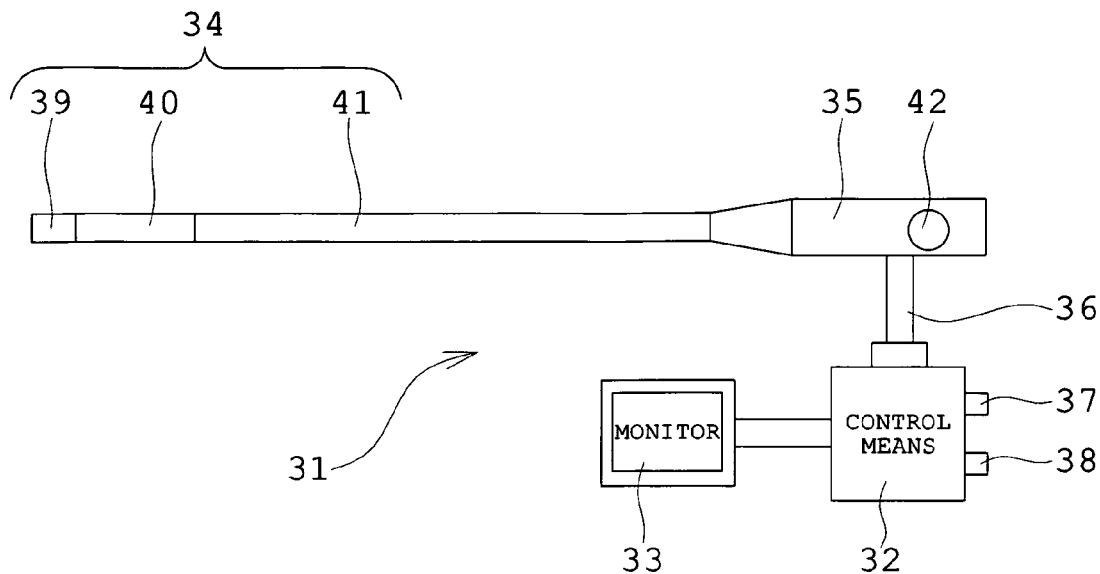
FIG. 9 is an explanatory diagram showing an outlined outside view of an endoscope apparatus as an optical apparatus equipped with the illumination light detecting optical system of the first embodiment according to the present invention.
Figure 10:
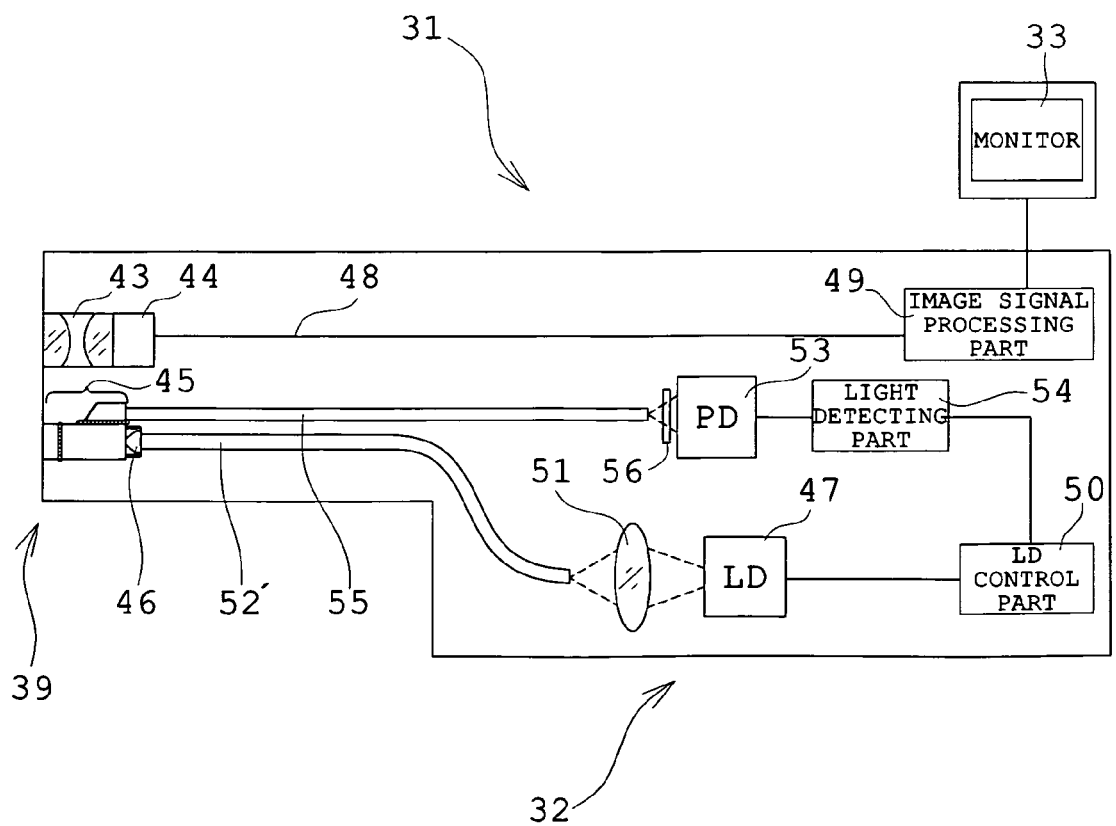
FIG. 10 is an explanatory diagram showing outlined constitution of the inside of the endoscope apparatus shown in FIG. 9.

Next, concrete embodiments of the optical apparatus equipped with the illumination light detecting optical system according to the implementation modes mentioned above will be shown. FIG. 9 is an explanatory diagram showing an outlined outside view of an endoscope apparatus as an optical apparatus equipped with the illumination light detecting optical system of the first implementation mode according to the present invention. FIG. 10 is an explanatory diagram showing outlined constitution of the inside of the endoscope apparatus shown in FIG. 9.

The endoscope apparatus 31 is constituted that it has a main part of the apparatus 32, a monitor 33 by which an image by the endoscope is displayed, an thin-long, flexible insertion part 34 which is inserted into a space to be examined, a control unit 35 gripped by an operator connected to a rear anchor in the inserting direction of the insertion part 34, and a universal cord 36 having flexibility extended from the control unit 35. In the main part of the apparatus 32, a main switch 37 which is a power switch of whole endoscope apparatus 31, and a lamp switch 38 which is a switch of a light source provided in the main part of the apparatus 32 are arranged.

In the insertion part 34, in order from the top side of the insertion part 34, a top part 39, a curving portion 40 formed by connecting two or more curving units so as to be rotated freely, and a long flexible tube part 41 formed by a flexible component are arranged in a series connection, and an end of base portion of the flexible tube part 41 is connected to a control unit 35. Here, the curving portion 40 may be curved by operating a curving operation knob 42 of the control unit 35. For example, it can be curved toward the upward and downward directions, or right and left directions. As shown in FIG. 4B, in the inside of the top part 39, an objective optical system 43 for making image forming of an observation image (an image to be observed) in an examination space, an imaging elements 44 such as CCD for converting the observation image in the examination space in which an image is formed by the objective optical system 43, into a video signal that is an electrical signal, an optical system 10 for illumination light detection, and a fluorescence luminescence component 46 which emits the illumination light for illuminating the inside of the examination space are arranged. The illumination light detecting optical system 45 and the fluorescence luminescence component 46 are constituted almost the same to the illumination light detecting optical system 10 of the first implementation mode and the fluorescence luminescence component 3, respectively, as shown in FIG. 3. The fluorescence luminescence component 3 emits mixed light, as illumination light, that is mixture of excitation light emanated from LD 47 and fluorescence excited by the excitation light, which will be mentioned later.

In the imaging element 44, a video signal line 48 is connected. The video signal line 48 transmits the video signal converted by the imaging element 44 to a video signal processing part 49 arranged at the main part 32 of the apparatus. The video signal processing part 49 converts the transmitted video signal into a TV signal, and outputs to monitor 33 as an image of endoscope. In the main part 32 of the apparatus, besides the video signal processing part 49, a light emitting element which is a light source for emitting excitation light, for example, laser diode (LD) 47, a LD controlling part 50 that is a light source controlling part for actuating control of the LD47, and a condensing optical system 51 for condensing excitation light having a short wavelength emanated from the LD47, for example, a blue color laser beam having wavelength of 445 nm are provided.

The laser beam emanated from the condensing optical system 51, in the insertion part 34 and the universal, cord 36, enters into the other end portion of the optical fiber for illuminating 52 that is a light guide for lighting. The optical fiber 52 is arranged so that one end portion may face to the fluorescence luminescence component 46 and the other end portion may face a focus of the condensing optical system 51. Here, the illumination light optical fiber 52 consists of single optical fiber. The laser beam entering into the other end of the illumination light optical fiber 52 is transmitted through the illumination light optical fiber 52, to the end side of the illumination light optical fiber 52, and then, it is irradiated to the fluorescence luminescence component 46. Fluorescent substance contained in the fluorescence luminescence component 46 emits fluorescence of red color light and green color light where the laser beam is used as excitation light. The fluorescence is mixed with the blue color light diffused within the fluorescence luminescence component 46, and it becomes the white color light that is used as illumination light, and then it is emitted in forward direction.

Further, as shown in FIG. 10, in the main part of the apparatus 32, a light detecting part 54 connected to a LD controlling part 50, a photodiode (PD) 53 which is a light sensor connected to the light detecting part 54, and an optical filter 56 that is a wavelength restricting component, which is arranged on an optical path of the light emanated from the other end of the light detecting optical fiber 55 between the other end of the light detecting optical fiber 55, and PD53 are arranged.

The optical filter 56 is a filter in which illuminating light that is extracted through the illumination light detecting optical system 45, and transmitted through the light detecting optical fiber 55, is transmitted while restricting the wavelength. The transmitted light is detected by PD 53. Concretely, it is a filter in which, from the illuminating light that is extracted through the illumination light detecting optical system 45, and transmitted through the light detecting optical fiber 55, blue color light which is excitation light is reflected or absorbed, and only fluorescence is transmitted. Then, the fluorescence is detected by PD 53. The PD 53 is constituted so that it may detect the fluorescence which is transmitted through the optical filter 56. The light detecting part 54 is constituted so that it may detect the intensity of the fluorescence detected in the PD 53 under control of the LD controlling part 30 which will be mentioned later.

Return light of illumination light which is emanated from the fluorescence luminescence component 46, and then deflected through the illumination light detecting optical system 45, in the insertion part 34 and the universal cord 36, enters into the end of the light detecting optical fiber 55. The light detecting optical fiber 55 is a light guide for detecting light which is arranged so that one end portion of it may face to the illumination light detecting optical system 45, and the other end portion may face the PD53. The light detecting optical fiber 55 is constituted with one optical fiber. Return light entering from the end of the light detecting optical fiber 55 is transmitted through the light detecting optical fiber 55 to the other end of the light detecting optical fiber 55, and then, enters into the optical filter 56. It is constituted such that after the return light enters into the optical filter 56, only the fluorescence is transmitted from the return light in the optical filter 56, and, then the fluorescence enters into the PD 53 and it is detected. Further, under control of actuating of the LD controlling part 50 that is controlling part, by the light detecting part 54, intensity of the fluorescence detected in the PD 53 is detected, and degradation of the fluorescence luminescence component 46 is detected from the intensity detected by the LD controlling part 50.

Then, operations of the endoscope apparatus of the first embodiment, which is constituted as mentioned above. Firstly, when a main switch 37 is turned on, the power source of the whole of the endoscope apparatus 31 is turned on. Then, an image of an examination object formed on the image pick-up element 44 in the examination space, is converted into a TV signal in the video signal processing part 49, and then, it is displayed on the monitor 33 as an image by the endoscope. When a lamp switch 38 is turned on in a state where the main switch 37 is turned on, a LD47 is actuated by actuation control of a LD controlling part 50, and then, blue color laser beam which is excitation light emanated from the LD47 enters into the fluorescence luminescence component 46 through the illumination light optical fiber 52. Then, fluorescence of red color light and fluorescence of green color light are emanated from the fluorescence luminescence component 46, where the blue color laser beam is performed as excitation light. The fluorescence is mixed with the blue color light diffused in the fluorescence luminescence component 46, and becomes white color light used as illumination light. The white color light is emitted by the illumination optical system 45 into the examination space, and then, the examination object is illuminated.

In this case, a part of the light emitted to forward direction from the fluorescence luminescence component 46 is returned to the PD53 side through the illumination optical system 45, and passes through the light-detecting-optical fiber 55, and then, it enters into the optical filter 56. Then, as for the return light, only fluorescence is transmitted through by the optical filter 56, the transmitted fluorescence enters into the PD 53. Namely, the fluorescence can be detected by the PD 53. Then, under control of actuating of the LD controlling part 50, the intensity of the fluorescence detected in the PD 53 is detected by the light detecting part 54, and degradation of the fluorescence luminescence component 46 is detected from the intensity detected by the LD controlling part 50. Concretely, in the light detecting part 54, when the intensity of fluorescence is not detected, or the intensity of the detected fluorescence is a predetermined value, and in detailed explanation, when it is less than the intensity of ordinary fluorescence used for examination of the inside of the examination space, for example, when the intensity that is less than a half is detected, it is detected by the LD controlling part 50, that the fluorescence luminescence component 46 has deteriorated. After this, by the LD controlling part 50, control of stopping of the irradiation of the laser beam from the LD47 is carried out, and actuation of the LD47 is stopped. Here, it is possible to control the LD47 so that the lighting of the LD47 may be done by an output such that the laser beam is not emanated from the LD47 without stopping it completely.

According to the endoscope apparatus of the embodiment 1, since the illumination optical system is constituted with the same as the illumination light detecting optical system of the first mode of implementation, while suppressing a light loss as much as possible, illumination light having the same ratio as that of the illumination light which illuminates an examination object as for a ratio of mixture of the fluorescence and the excitation light and illumination light, can be detected with high precision. Furthermore, in the endoscope apparatus of the embodiment 1, an optical filter 56 which reflects or absorbs blue color light from the return light of the illumination light, and transmits only fluorescence, is arranged between the other end of the light detecting optical fiber 55 in the main part of the apparatus 32 and the PD53, on the optical path of the light emanated from the other end of the light detecting optical fiber 55, and, further the PD53 which detects the fluorescence transmitted by the optical filter 56, and a light detecting part 54 which detects the intensity of fluorescence are arranged. Further, the LD controlling part 50 which detects degradation of the fluorescence luminescence component 46, and controls an actuation for stopping of the irradiation of the laser beam from the LD47, based on the detection of the degradation. Accordingly, even though the fluorescence luminescence component 46 has deteriorated, degradation of the fluorescence luminescence component 46 can be detected surely through the light detecting optical fiber 55, the optical filter 56, the PD53, and the light detecting part 54. Therefore, according to the endoscope apparatus of the embodiment 1, fall in the intensity of fluorescence, or failure of irradiation of the fluorescence can be detected surely by the degradation of the fluorescence luminescence component.

In the present embodiment, although blue color laser beam is used as excitation light emanated from the LD47, it is not limited to only this. As long as it is excitation light with a short wavelength, for example, ultra-violet light can be used. In this case, white color light can be obtained by using a fluorescent substance which emits blue color light also. Moreover, the semiconductor light emitting element is not limited to LD. As long as it is a semiconductor light emitting element of low power, for example, any of light emitting diode (LED) etc., can be used.

In the present embodiment, it constituted so that emitting of the laser light from LD47 may be stopped when degradation of the fluorescence luminescence component 46 is detected by the LD controlling part 50. However, in addition to this, when the degradation of the fluorescence luminescence component 46 is detected, by controlling actuation of the LD controlling part 50 so that an alarm, a warning sign, etc. may be output, it is possible to notify of the degradation of the fluorescence luminescence component 46 to a user. Furthermore, in the present embodiment, it is constituted so that the LD controlling part 50 may detect the degradation of the fluorescence luminescence component 46. However, it is not limited to this example only. When detection of fluorescence is not made by the PD53, the LD controlling part 50 can detect also an breakage of the illumination light optical fiber 52. In the present embodiment, although the light detecting optical fiber 55 and the illumination light optical fiber 52 which are light guides are constituted with one optical fiber respectively, it is not limited to this case. It can be constituted with an optical fiber bundle which bundles two or more optical fibers.

Figure 11:
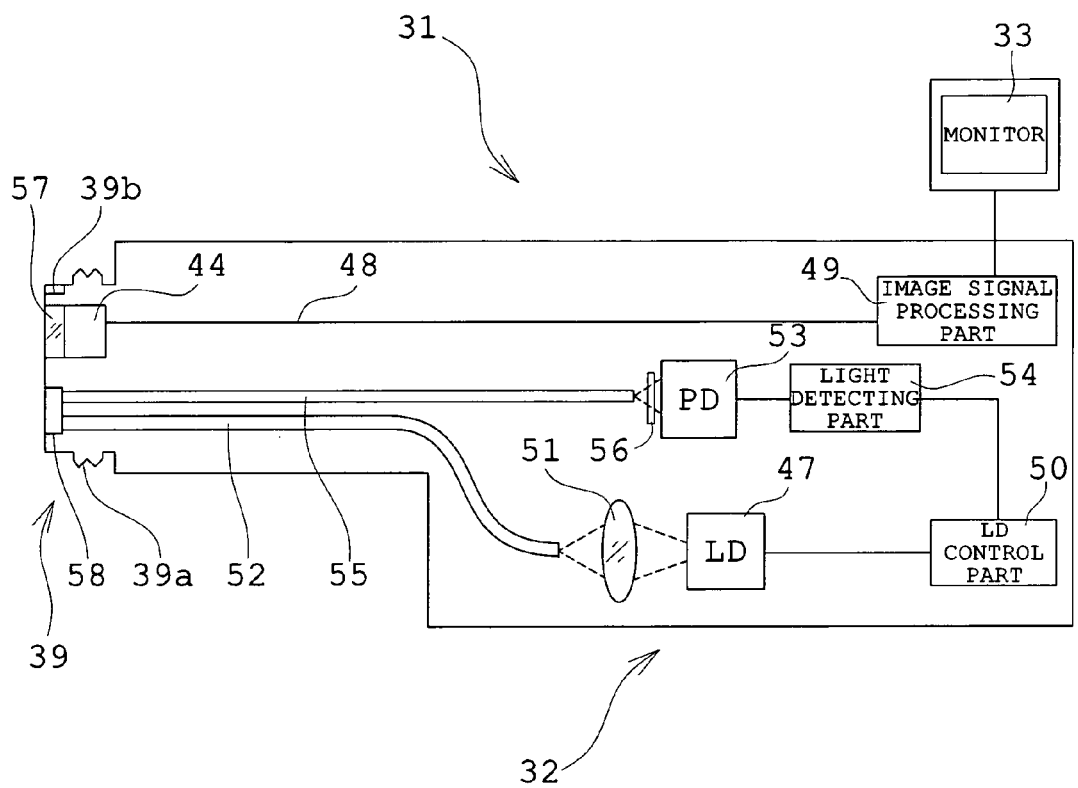
FIG. 11 is an explanatory diagram showing an outlined modified example of the constitution of the inside of the endoscope apparatus shown in FIG. 9. Here, as for only the top portion of an insertion part, its sectional view is shown.
Figure 12:
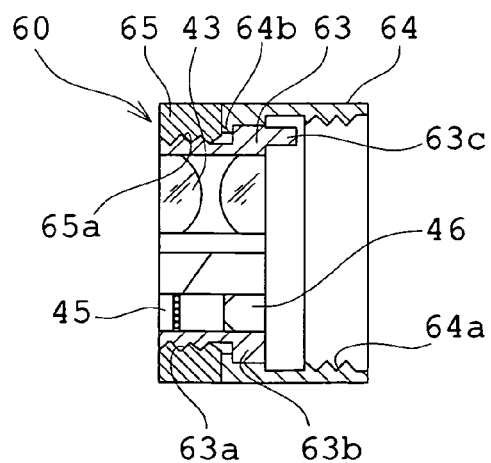
FIG. 12 is a partial sectional view showing an optical adapter which can be detached and attached freely to the top portion of the insertion part of the endoscope apparatus shown in FIG. 11.
Figure 13:
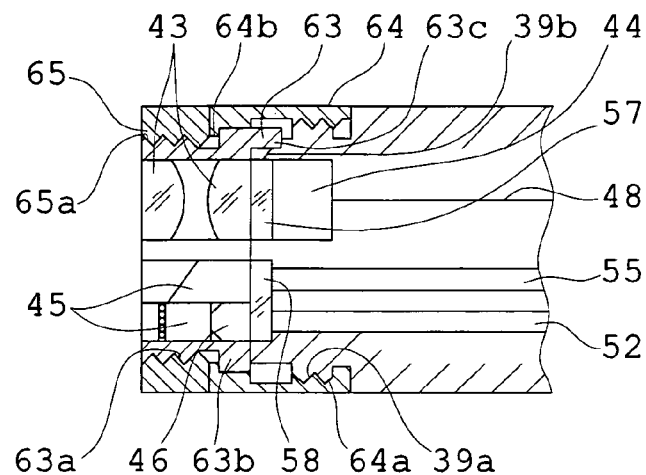
FIG. 13 is a partial sectional view showing a state in which an optical adapter shown in FIG. 12 is put into the top portion of the insertion part of the endoscope apparatus shown in FIG. 9.

The other modified examples will be explained using FIGS. 11-13. FIG. 11 is an explanatory diagram showing outlined modified example of the constitution of the inside of the endoscope apparatus shown in FIG. 9. (showing a cross section of the top part of the insertion portion only). FIG. 12 is a partial sectional view showing an optical adapter which can be attached freely to the top portion of the insertion part of the endoscope apparatus shown in FIG. 11. FIG. 13 is a partial sectional view showing a state in which the optical adapter in FIG. 12 is put in the top portion of the insertion part of the endoscope apparatus shown in FIG. 11

In the endoscope apparatus of the modified example of the embodiment 3, as shown in FIG. 11, a male screw 39a is formed on a perimeter of the top part 39. Furthermore, at the perimeter of the top part 39, which is at a forward side from the male screw 39a, a positioning groove 39b is formed. The male screw 39a is a screw for equipping the top part 39 with the optical adapter 60. In the inside of the top part 39, an image pick-up element 44, and top parts of the illumination light optical fiber 52 and the light detecting optical fiber 55 are arranged. The image pick-up element 44 is protected by an image pick-up element cover glass 57, and the top side of the illumination light optical fiber 52 and the light detecting optical fiber 55 are protected by an optical fiber cover glass 58.

As shown in FIG. 12, the principal part of the optical adapter 60 is constituted with an adapter main body 63 having nearly tubular shape, a retaining ring 64 having nearly cylindrical shape, and a stop part 65. In the inside of the main part of the adapter 63, the objective optical system 43 for forming an image of an observation image of the examination object on the image pick-up element 44, the fluorescence luminescence component 46 which emits fluorescence where the laser light from the LD47 is used as excitation light, and the illumination light detecting optical system 45 in which the illumination light of white color light emanated from the fluorescence luminescence component 46 is emitted into the examined space and a part of the light is made to return to the PD53 side are arranged. The illumination light detecting optical system 45 and the fluorescence luminescence component 46 are constituted almost similar to the illumination light detecting optical system 10 and the fluorescence component 3 of the first implementation mode shown in FIG. 3, respectively.

On the top part side perimeter of the main part of the adapter 63, a male screw 63a is formed. The male screw 63a is screwed to a female screw 65a formed in the inner circumference of the stop member 65. On the insertion-part side perimeter of the main body of the adapter 63, a connecting part 63b for engaging to the retaining ring 64 is formed. And, by engaging the connecting part 63b to the adapter connecting part 64b formed in inner circumference of the top part side of the retaining ring 64, the retaining ring 64 is constituted so as to be rotated freely to the main part of the adapter 63. Furthermore, it is constituted so that the retaining ring 64 may not separate from the main part of the adapter 63 by arrangement that the screw part of the female screw 65a of the stop member 65 and the male screw 63a of the main part of an adapter 63 are fixed with adhesives. The female screw 64a is formed on the inner circumference of the insertion part 34 of the retaining ring 64. The female screw 64a is screwed to the male screw 39a of the perimeter of the top part 39, and thus the top part 39 is mounted on the optical adapter 60.

On a surface of the insertion-part 34 of the main body of the adapter 63, a positioning projection 63c is formed. When the top part 39 is mounted on the optical adapter 60, the positioning projection 63c is fitted into the positioning groove 39b of the top part 39, and, thus the rotation to the top part 39 of the main part of the adapter 63 is regulated. Thereby, when the top part 39 is mounted on the optical adapter 60, the objective optical system 43 is arranged at a position which faces the imaging element 44, and an exit surface at PD53 side of the illumination light detecting optical system 45, and the fluorescence luminescence component 46 are arranged respectively, at the position where they face the top part sides of the light-detecting-optical fiber 55 and the optical fiber for illuminating 52.

As shown in FIG. 13, in the state that the top part 39 is mounted on the optical adapter 60, the female screw 64a of the inner circumference of the retaining ring 64 and the male screw 39a of the perimeter of the top part 39 are screwed, and the positioning projection 63c of the main part of the adapter 63 and the positioning slot 39b of the top part 39 are screwed. Thus, by constituting such that the optical adapter 60 is arranged so that it can be attached and detached freely to the top part 39, characteristics of the objective optical system 43 can be changed by exchanging the optical adapter 60. Thus, as to photographic or examination object, optimum angle of view, observation direction, and depth of focus can be chosen. Other constitutions are the same as those of the example of FIG. 10.

In a state that the optical adapter 60 is mounted, the laser beam which is excitation light emanated from LD47 is irradiated to the fluorescence luminescence component 46 through the condensing optical system 51, the illumination-optical fiber 52, and the optical fiber cover glass 58. The white color light that is the illumination light emanated toward the forward direction from the fluorescence luminescence component 46 is emitted into the examination space through the illumination light-detecting-optical system 45, and a part of light is returned to the PD53 side. The return light is detected by the PD53 after it is transmitted through the light-detecting-optical fiber 55, and only fluorescence is extracted by the optical filter 56. Then, the intensity of the fluorescence is detected by the light detecting part 54 under control of actuating of the LD controlling part 50.

Thus, in such constitution that the fluorescence luminescence component 46 is arranged at the optical adapter 60, the white color light that is illumination light is no longer emitted, since a laser beam is no longer irradiated by the fluorescence luminescence component 46 from LD47 if the optical adapter 60 is removed from the top part 39. Accordingly, the fluorescence is no longer detected in the PD53. Thus, since actuation control for stopping of radiation of the laser beam from the LD47 is done by the LD controlling part 50, the user can detach and attach the optical adapter 60 to the top part 39 without feeling dazzle, and accordingly, operability improves. As mentioned above, even if the actuation control of the LD47 is carried out so that the actuation of LD47 may not be stopped completely, and the light may be switched on by an output that laser beam is not emanated from the LD47, the same effect can be obtained.

By exchanging the optical adapter 60, the fluorescence luminescence component 46 can be exchanged to the fluorescence luminescence component having another characteristics, and a wavelength of the light for illuminating the inside of examination object space can be changed easily. Therefore, the user can choose illumination having a wavelength suitable for the examination object. Other constitutions are the same as those of the example of FIG. 10. As for attachment and detachment to the top part 39 of the optical adapter 60, it is not limited to the locking means by screw threads mentioned above. Other fixing means by such as screw stop, connection by depressed and projected portion, etc., can be used.

Embodiment 2

Figure 14:
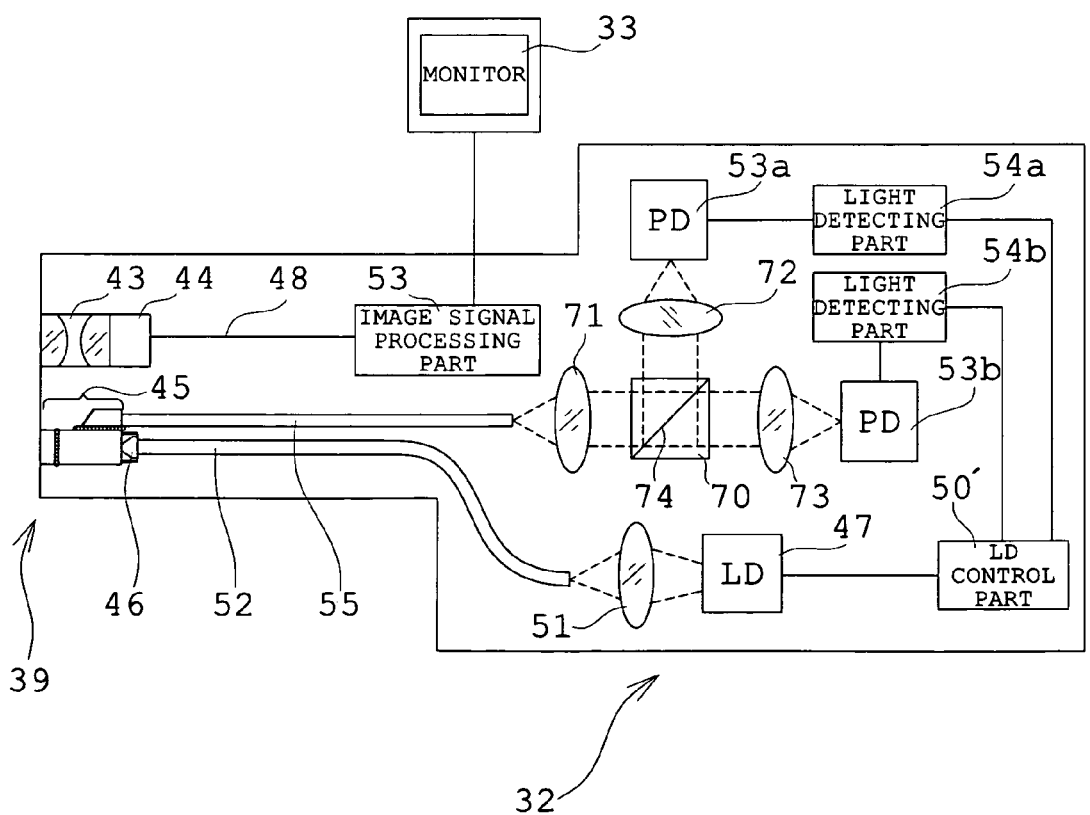
FIG. 14 is an explanatory diagram showing an outlined inside view of an endoscope apparatus as an optical apparatus equipped with the illumination light detecting optical system of the embodiment 2 according to the present invention.

FIG. 14 is an explanatory diagram showing an outlined inside view of an endoscope apparatus as an optical apparatus equipped with the illumination light detecting optical system of the embodiment 2 according to the present invention. The endoscope apparatus of the embodiment 2 differs in that the return light of the illumination light is detected by two PD comparing with the endoscope apparatus 1 shown in FIGS. 9 and 10. Here, only differences will be explained. The same symbols are used to the same constitution in the embodiment 1, and the explanation of the same constitution will be omitted. As shown in FIG. 14, in the main part of the apparatus 32, light detecting parts 54a and 54b that are connected to a LD controlling part 50' that is a light source controlling part; a photodiode (PD) 53a connected to the light detecting part 54a; a photodiode (PD) 53b connected to the light detecting part 54b; and an optical splitter 70 (a wavelength restricting component) arranged between the other end of the light detecting optical fiber 55 and PD 53a, PD 53b; are arranged.

At an input end side of the light splitter 70, concretely, at a position facing to the other end of the light detecting optical fiber 55, a condensing optical system 71 is arranged. In one of output end sides of the light splitter 70 the condensing optical system 72 is arranged. In another of output end sides of the light splitter 70 the condensing optical system 73 is arranged. Near the focus position of the condensing optical system 72 the PD53a is arranged, and near the focus point of the condensing optical system 73 the PD53b is arranged. The condensing optical system 71 condenses the return light of the illumination light emanated from the light detecting optical fiber 55, and makes it enter into the light splitter 70. The condensing optical system 72 condenses the fluorescence emanated from the light splitter 70, and makes it enter into the PD53a. The condensing optical system 73 condenses the excitation light emanated from the light splitter 70, and makes it enter into the PD53b. The light splitter 70 is formed so as to have a cubic shape in which slopes of two rectangular prisms are joined.

On a slope of one of the prisms of the light splitter 70, a reflective thin film 74 having wavelength selectivity is formed by vapor-deposition. The reflective thin film 74 is constituted with either of a thin film which transmits excitation light and reflects the fluorescence, or a thin film which reflects the excitation light and transmits the fluorescence, out of the return light of the illumination light. In the following explanation, the reflective thin film 74 is a thin film which transmits the excitation light and reflects the fluorescence. In this case, the PD53a functions the first light sensor that detects only fluorescence, and the PD53b constitutes the second light sensor that detects only excitation light.

In the light splitter 70 constituted as mentioned above, at least, the return light is transmitted, otherwise it is reflected by restricting a wavelength of the return light of the illumination light, and the excitation light and the fluorescence which have been transmitted or reflected are detected by different PD, respectively. Concretely, in the light splitter 70, the blue color light that is excitation light is transmitted toward the PD53b, and then the blue color light is detected by the PD53b. In meanwhile, the fluorescence is reflected toward the PD53a, and then the fluorescence is detected by the PD53a. In the light detecting part 54a, the intensity of the fluorescence detected in the PD53a is detected under the actuation control of LD-controlling part 50'. The light detecting part 54b detects the intensity of the excitation light detected in the PD33b under the actuation control of the LD-controlling part 50'. In the LD-controlling part 50', the intensity of the fluorescence detected in the PD53a is detected under the actuation control of the light detecting part 54a, In meanwhile, the intensity of the fluorescence detected in the PD 53b is detected by actuating of control of the light detecting part 54b, and the intensity of the fluorescence to the intensity of the excitation light is detected. By this way, degradation of the fluorescence luminescence component 46 can be detected.

Concretely, in the light detecting part 54a, when the intensity of fluorescence is not detected, or, when the intensity of the fluorescence to the intensity of the detected excitation light is a predetermined value, when in detail, it is less than the intensity of the fluorescence used for inspecting the examination object space, for example, when the intensity less than a half of ordinary value is detected, by the LD-controlling part 50', it is detected that the fluorescence luminescence component 46 has deteriorated. Then, the actuation control for stopping of radiation of the laser beam from LD47 is carried out by the LD-controlling part 50', and the actuation of LD47 is stopped. Here, without stopping the actuation of the LD47 completely, the actuation control of the LD47 can be carried out so that the light may be switched on by an output such that laser beam is not emanated from the LD47.

Then, operations of the endoscope of the embodiment 2, which is constituted as mentioned above will be explained briefly. In the embodiment 2, as to explanation concerning the emission of radiation of the laser beam by the LD 47 to the return light of the illumination light emanated from the other end of the light-detecting-optical fiber 55 is the same as that of the first embodiment mentioned above. Therefore, the explanation will be omitted. The return light emanated from the end of the light detecting optical fiber 55 is condensed by the condensing optical system 71, and it enters into the light splitter 70. Then, in the light splitter 70, the blue color light that is excitation light is transmitted toward the PD 53b, and then the transmitted blue color light is condensed by the condensing optical system 73, and it is emitted toward the PD53b and detected by PD 53b. And, the fluorescence is reflected toward the PD 53a, and then the reflected fluorescence is condensed by the condensing optical system 72, and it is detected by the PD 53a.

Then, under control of actuating of the LD controlling part 30, the intensity of fluorescence is detected by the light detecting part 54a, the intensity of the blue color light is detected by the light detecting part 54b. Then, the intensity of the fluorescence to the intensity of the blue color light is detected by the LD-controlling part 50'. Thereby, degradation of the fluorescence luminescence component 46 can be detected. Then, when the degradation of the fluorescence luminescence component 46 is detected, control which drives LD 47 is carried out so that control for stopping of radiation of the laser beam from LD 47 may be carried out, or the light may be switched on by an output that laser beam is not emanated from the LD 47 by the LD-controlling part 50'.

Thus, in the endoscope apparatus of the embodiment 2, by the light splitter 70, the fluorescence and excitation light are separated from the return light, and the fluorescence and the excitation light are detected separately by the PD 53a and 53b, respectively. In meanwhile, in the LD-controlling part 50', by actuating of control of the other light detecting parts 54a' and 54b, the intensity of fluorescence and the excitation light are measured, respectively, and the intensity of the fluorescence to the intensity of the excitation light is detected. By this way, degradation of the fluorescence luminescence component 46 can be detected.

According to the endoscope apparatus of the embodiment 2, that is the same as the endoscope apparatus of the embodiment 1, the illumination optical system is constituted like the illumination light detecting optical system of the embodiment 1. Accordingly, while suppressing light loss as much as possible, as for a ratio of mixture of the fluorescence light and the excitation light, the illumination light having the same ratio as that of the illumination light which illuminates the examination object can be detected with high precision. According to the endoscope apparatus of the embodiment 2, since the fall of the intensity of fluorescence is detected by using two parameters of the intensity of fluorescence and the intensity of the excitation light, degradation of the fluorescence luminescence component 46 can be detected with higher precision than that of the endoscope apparatus of the embodiment 1. For this reason, according to the endoscope apparatus of the embodiment 2, the fall of the intensity of the fluorescence or the non-illumination of fluorescence by the degradation of a fluorescence luminescence component can be detected with high precision.

In the LD-controlling-part 50', by detecting only the intensity of the excitation light detected in the PD53b under the actuation control of the light detecting part 54b, breakage of the illumination-optical fiber 52 or the LD 47 can be detected. In that case in the LD-controlling part 50', after detecting the breakage of the illumination-optical fiber 52 or the LD47, actuation control for stopping the LD 47 completely is carried out. As for distinctly judging of the degradation of the fluorescence luminescence component 46, and the breakage of the illumination-optical fiber 52 or the LD 47, as mentioned above, it can be done as follows. Namely, after the degradation of the fluorescence luminescence component 46 is detected, control of the LD 47 is actuated so that the light may be switched on by an output that laser beam is not emanated from the LD 47, without stopping the actuation of the LD47 completely. Under such state, when LD 47 is being actuated even if the laser beam is not emitted, the user can judge it as degradation of the fluorescence luminescence component 46, and when the actuation of the LD 47 stops completely, the user can judge it as breakage of the illumination-optical fiber 52 or the LD 47. Thus, according to the endoscope apparatus of the embodiment 2, the fluorescence luminescence component 3, and the breakage of the illumination-optical fiber 52 or the LD47 can be detected distinctly.

In the example of FIG. 14, as the reflective thin film 74, a thin film which transmits the excitation light and reflects the fluorescence is used. However, as the reflective thin film 74, the thin film which reflects the excitation light and transmits the fluorescence can be used. In this case, the condensing optical system 72 condenses the excitation light emanated from the light splitter 70, and the condensed excitation light enters into the PD53a, and other hand, the condensing optical system 73 condenses the fluorescence emanated from the light splitter 70, and the condensed fluorescence enters into the PD53b. The PD53a functions the second light sensor that detects only excitation light, and the PD53b functions the first light sensor that detects only fluorescence, Thus, in the light splitter 70, the fluorescence is transmitted toward the PD53b, and the fluorescence is detected by PD53b, and in meanwhile, the excitation light is reflected toward the PD53a and it is detected by the PD53a. The light detecting part 54b detects the intensity of the excitation light detected in the PD53b under the actuation control of the LD-controlling-part 50'. The light detecting part 54b detects the intensity of the fluorescence detected in the PD53b under the actuation control of the LD-controlling-part 50'.

Also in the embodiment 2, as for the excitation light having a short wavelength, it is not limited to blue color laser beam, and for example, ultra-violet light can be used. As for the semiconductor light emitting element, it is not limited to LD, and as long as it is a semiconductor light emitting element of low power, for example, light emitting diode (LED) etc. may be used. Further, it may be constituted such that in the LD-controlling-part 50', after degradation of the fluorescence luminescence component 46 is detected, by actuation control which issues beeping, a warning sign, etc., the degradation of the fluorescence luminescence component 46 is notified to the user. Further, also in the endoscope apparatus of the embodiment 2, like the modified examples of the embodiment 1 shown in FIGS. 11-13, it may be constituted such that the optical adapter 60 may be detached and attached freely to the top part 39 of the insertion part 34. Effects in this case are almost the same as the example of the modified example shown in FIGS. 11-13.

Embodiment 3

Figure 15:
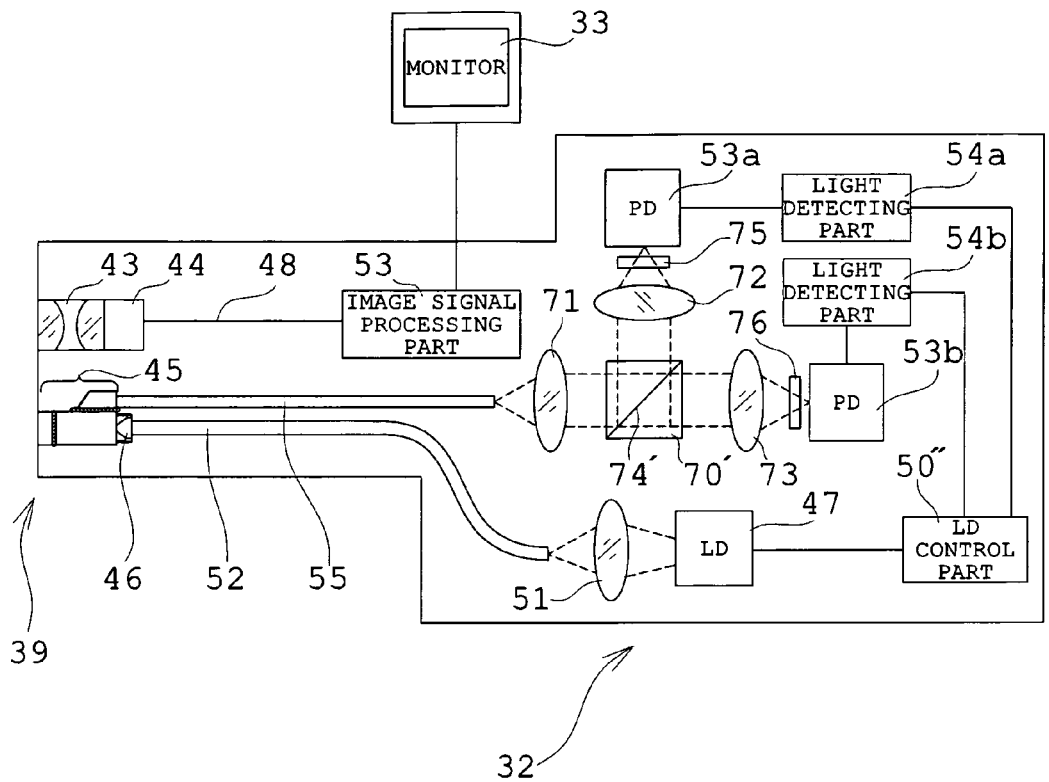
FIG. 15 is an explanatory diagram showing an outlined inside view of an endoscope apparatus as an optical apparatus equipped with the illumination light detecting optical system of an embodiment 3 according to the present invention.

FIG. 15 is an explanatory diagram showing an outlined inside view of an endoscope apparatus as an optical apparatus equipped with the illumination light detecting optical system of an embodiment 3 according to the present invention. The endoscope apparatus of the embodiment 3 differs in that the light splitter is constituted with a mere half mirror in which the return light is divided in two directions without restricting wavelength to the return light which enters into the light splitter, in comparison with the endoscope apparatus shown in FIG. 13. Here, only this difference will be explained, the same symbols are used to the same constitution as the embodiment 1 and the embodiment 2, and the explanation will be omitted.

As shown in FIG. 15, in the main part of the apparatus 32, a light detecting parts 54a and 54b that are connected to a LD controlling part 50" that is a light source controlling part; a photodiode (PD) 53a connected to the light detecting part 54a; a photodiode 53b connected to the light detecting part 54b; a first optical filter 75 which is a wavelength restriction component; a second optical filter 76 which is a wavelength restriction component; and the light-splitter 70' are arranged. At an input end side of the light splitter 70', concretely, at a position facing to the other end of the light detecting optical fiber 55, a condensing optical system 71 is arranged. In one of output end sides of the light splitter 70', the condensing optical system 72 is arranged. In another output end side of the light splitter 70, the condensing optical system 73 is arranged.

Near the focus point of the condensing optical system 72, and between the condensing optical system 72 and the PD53a, the first optical filter 75 is arranged, and near the focus point of the condensing optical system 73, and between the condensing optical system 73 and the PD53b, the second optical filter 76 is arranged. In the condensing optical system 71, the return light of the illumination light emanated from another end of the light-detecting-optical fiber 55 is condensed, and the condensed light enters into the light splitter 70. In the condensing optical system 72, the return light emanated from the light splitter 70' is condensed, and it enters into the first optical filter 75. In the condensing optical system 73, the return light emanated from the light splitter 70', and enters into the second optical filter 76. The light-splitter 70' is constituted to be a cubic shape in which slopes of two rectangular prisms are joined. In the light-splitter 70', a reflective thin film 74' having wavelength selectivity is formed by vapor-deposition on the slope of one of the prisms. The reflective thin film has a function as a mere half mirror for separating the return light of the illumination light, which enters into the slope, into the PD53a and the PD53b, respectively, The PD53a is the first light sensor that detects only fluorescence, the PD53b is the second light sensor that detects only excitation light. The optical filter 75 is a filter in which the wavelength of the return light of the illumination light separated by the light-splitter 70' is transmitted under restriction, and the return light transmitted is detected by the PD 53a. Concretely, it is a filter in which only the fluorescence is transmitted, and the transmitted fluorescence is detected by the PD 53a. The optical filter 76 is a filter in which the wavelength of the return light of the illumination light separated by the light-splitter 70' is transmitted under restriction, and the return light transmitted is detected by the PD53b. Concretely, it is a filter in which only the blue color light that is the excitation light is transmitted, and the transmitted blue color light is detected by the PD53b.

In the light detecting part 54a, the intensity of the fluorescence detected in the PD53a is detected under the actuation control of LD-controlling part 50". In the light detecting part 54b, the intensity of the excitation light detected in the PD53b is detected under the actuation control of LD-controlling part 50". In the LD-controlling part 50", the intensity of the fluorescence detected in the PD53a is detected by using the light detecting part 54a, and the intensity of the fluorescence detected in the PD 53b is detected by using the light detecting part 54b, and then by detecting the intensity of the fluorescence to the intensity of the excitation light, degradation of the fluorescence luminescence component 46 can be detected. Concretely, when the intensity of fluorescence is not detected in the light detecting part 54a, or when the intensity of the fluorescence to the intensity of the detected excitation light of a predetermined value is detected. Specifically, when the intensity less than the intensity of the fluorescence used for the inspection in examination object space is detected, for example, when the intensity less than a half of ordinary value is detected, it is detected that the fluorescence luminescence component 46 has deteriorated by the LD-controlling part 50". Then, the actuation control for stopping of radiation of the laser beam from the LD47 is carried out by the LD-controlling part 507', and the actuation of LD47 is stopped. The control of the LD47 may be actuated so that the light may be switched on by an output that laser beam is not emanated from the LD47, without stopping the actuation of the LD47 completely.

Next, operations of the endoscope of the embodiment 3 constituted as mentioned above will be explained. Since as for operations they are the same as these of the embodiment 1 as to the operations from emitting of the laser beam by LD47 to emitting the return light of an illumination light by the other end of the light-detecting-optical fiber 55, the explanation will be omitted.

Return light which is emanated from the other end of the light detecting optical fiber 55 is condensed by the condensing optical system 71, and the condensed light enters into the light splitter 70'. Then, in the light-splitter 70', the return light is separated towards the PD53a and 53b, and one of the return light is condensed by the condensing optical system 72, and then, it is emitted towards the PD53a, and only the fluorescence is detected by the PD53a after only fluorescence is transmitted by the first optical filter 75. In meanwhile, another the return light is condensed by the condensing optical system 73, it is emitted towards the PD53b, and only the excitation light is detected by the PD53b after only the excitation light is transmitted by the second optical filter 76.

Then, by the light detecting part 54a under control of actuating of the LD controlling part 50", the intensity of fluorescence is detected, and the intensity of the excitation light is detected by the light detecting part 54b. Then, by the LD-controlling-part 50", the intensity of the fluorescence to the intensity of the excitation light is detected. Thereby, the degradation of the fluorescence luminescence component 46 can be detected. Then, when the degradation of the fluorescence luminescence component 46 is detected, the actuation control for stopping of radiation of the laser beam from LD47 is carried out by the LD-controlling part 50", otherwise the actuation control of the LD47 is carried out so that the light may be switched on by an output by which the laser beam is not emanated from the LD47.

According to the endoscope apparatus of the embodiment 3, since the illumination optical system is constituted like the illumination light detecting optical system of the embodiment 1, and like in the endoscope apparatus of the embodiment 1, while suppressing a light loss as much as possible, the illumination light having the same ratio as that of the illumination light which illuminates the examination object as to a ratio of mixture of the fluorescence light and the excitation light can be detected with high precision. Also, in the endoscope apparatus of the embodiment 3, in the LD-controlling-part 50", only the intensity of the excitation light detected in the PD 53b is detected by using the light detecting part 54b. By this way, breakage of the illumination-optical fiber 52 or LD47 can be detected. At that time, in the LD-controlling-part 50", after detecting the breakage of the illumination-optical fiber 52 or the LD47, actuation control for stopping the LD47 completely is carried out.

The degradation of the fluorescence luminescence component 46, and the breakage of the illumination-optical fiber 52 or the LD47 can be distinctly judged as follows. As mentioned above, after the degradation of the fluorescence luminescence component 46 is detected, actuation control of the LD47 is carried out so that the light may be switched on by an output that laser beam is not emanated from the LD47 without stopping the actuation of the LD47 completely. In this state, when LD47 is being actuated even if the laser beam is not emitted, the user can judge of the degradation of the fluorescence luminescence component 46, and when the actuation of the LD47 stops completely, the user can judge of the breakage of the illumination-optical fiber 52 or the LD47. Thus, also in the endoscope apparatus of the embodiment 3, the fluorescence luminescence component 3, and the breakage of the illumination-optical fiber 52 or LD47 can be distinctly detected.

Thus, in the endoscope apparatus of the embodiment 3, as excitation light with a short wavelength, it is not limited to blue color laser beam. For example, ultra-violet light can be used. As to a semiconductor light emitting element is not limited to LD, As long as it is a semiconductor light emitting element of low power, for example, light emitting diode (LED) etc. may be used. In the LD-controlling-part 50", after the degradation of the fluorescence luminescence component 46 is detected, by actuating control so as to output beeping, a warning sign, etc., the degradation of the fluorescence luminescence component 46 can be informed to the user. Further, also, in the endoscope apparatus of the embodiment 3, as same as the modified examples of the embodiment 1 shown in FIGS. 11-13, it is possible to adopt a constitution such that optical adapter 60 can be detached and attached freely to the top part 39 of the insertion part 34. Effects in this case, are almost the same as these of the example of the modified embodiment shown in FIGS. 11-13.

Embodiment 4

Figure 16:
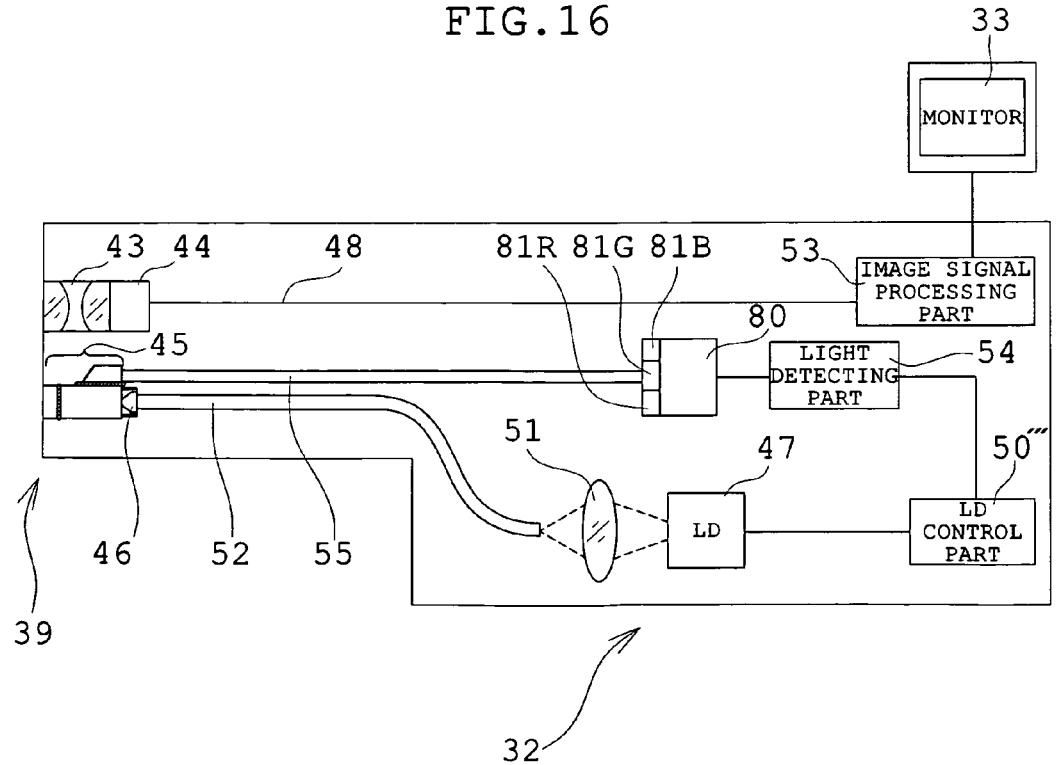
FIG. 16 is an explanatory diagram showing an outlined inside view of an endoscope apparatus as an optical apparatus equipped with the illumination light detecting optical system of an embodiment 4 according to the present invention.

FIG. 16 is an explanatory diagram showing an outlined inside view of an endoscope apparatus as an optical apparatus equipped with the illumination light detecting optical system of a fourth embodiment according to the present invention. The endoscope apparatus of the embodiment 4, comparing with the endoscope apparatus shown in FIGS. 9 and 10, differs in that in a RGB color sensor in which three channels of PD combined with color filters which have sensitivity of blue, green, and red color, respectively are packed to one, the return light of the illuminating light is transmitted by dividing into green color and red color fluorescence, and blue color excitation light. Here, only differences will be explained. The same symbols are used to the same constitutions in the embodiment 1, and, explanation of the same constitution will be omitted.

As shown in FIG. 16, in the main part of the apparatus 32, a light detecting part 54 connected to a LD controlling part 50''' that is a light source controlling part, and a RGB color sensor 80 which is a light sensor connected to the light detecting part 54 is arranged. The RGB color sensor 80 is a color sensor in which three channels of PD combined with color filters 81R, 81G, 81B which have sensitivity of blue color, green color, and red color, respectively, of the return light of the illumination light are packed to one. The red color filter 81R, and the green color filter 81G are filters in which the return light of the illuminating light is transmitted while restricting the wavelength, and the return light after transmitted is detected by the RGB color sensor 80. Concretely, they are the first wavelength restricting components in which the blue color excitation light is reflected or absorbed from the return light, and only the red and green color fluorescence are transmitted, respectively, and then the fluorescence is detected by the RGB color sensor 80.

The blue color filter 81B is a filter in which the return light of the illuminating light is transmitted while restricting the wavelength, and the return light after transmitted is detected by the RGB color sensor 80. Concretely, it is the second wavelength restricting component in which the red and green color fluorescence are reflected or absorbed from the return light, and only the blue color excitation light is transmitted, and then the blue color excitation light is detected by the RGB color sensor 80. In the light detecting part 54, the intensity of the fluorescence and excitation light detected in the RGB color sensor 80 are detected under the actuation control of LD-controlling-part 50'''. In the LD-controlling-part 50''', the intensity of the fluorescence and excitation detected in the color filter 80 are detected by using the light detecting part 54, and then by detecting the intensity of the fluorescence to the intensity of the excitation light, degradation of the fluorescence luminescence component 46 can be detected.

Concretely, in the RGB color filter 80, when the intensity of fluorescence is not detected, or, when the intensity of the fluorescence to the intensity of the detected excitation light is a predetermined value, more concretely, when it is smaller than the intensity of the fluorescence used for inspecting the examination object space, for example, when the intensity smaller than a half of ordinary value is detected, it is detected that the fluorescence luminescence component 46 has deteriorated by the LD-controlling-part 50'''. Then, actuation control for stopping of radiation of the laser beam from the LD47 is carried out by the LD-controlling-part 50'''. Concretely, the actuation of the LD47 is stopped. Here, the control of the LD47 can be actuated so that the light may be switched on by an output by which the laser beam is not emitted from the LD47 without stopping the actuation of the LD47 completely.

Next, operations of the endoscope of the embodiment 4 constituted as mentioned above, will be explained. Also in the embodiment 4, as to explanation concerning the process from emitting of radiation of the laser beam by the LD47 to the return light of the illuminating light emitted from the other end of the light-detection-optical fiber 55, it is the same as that of the embodiment 1 mentioned above. Therefore, the explanation of the same constitution will be omitted. Return light which is emanated from the other end of the light detecting optical fiber 55 is emitted to the RGB color filter 80. Then, in the RGB color filter 80, via the red color filter 81R and the green color filter 80G, only the red and green color fluorescence are transmitted by each filter from the return light, and the fluorescence is detected by the RGB color sensor 80. In meanwhile, via the blue color filter 81B, only the blue color excitation light is transmitted from the return light, and then the excitation light is detected by the RGB color sensor 80.

Then, the intensity of fluorescence and the intensity of excitation light are detected by the light detecting part 54 under control of actuating of the LD controlling part 50'''. Then, by the LD-controlling-part 50''', the intensity of the fluorescence to the intensity of the excitation light is detected. Thereby, the degradation of the fluorescence luminescence component 46 is detected. Then, when the degradation of the fluorescence luminescence component 46 is detected, actuation control for stopping of radiation of the laser beam from the LD47 is carried out by the LD-controlling-part 50''', otherwise, actuation control of the LD47 is carried out so that the light may be switched on by an output in which the laser beam is not emitted from the LD47.

According to the endoscope apparatus of the embodiment 4, since the illumination optical system is constituted like the illuminating light detection optical system of the embodiment 1 as well as such constitution is adopted in the endoscope apparatus of the embodiment 1, the illuminating light having the same ratio as that of the illuminating light which illuminates the examination object as to a ratio of mixture of the fluorescence light and the excitation light can be detected with high precision while suppressing a light loss as much as possible. Also, in the endoscope apparatus of the embodiment 4, in the LD-controlling-part 50''', by detecting only the intensity of the blue color excitation light detected in the RGB color sensor 80 by using the light detecting part 54, breakage of the illumination-optical fiber 55 or the LD47 can be detected. In this case, in the LD-controlling part 50''', after detecting the breakage of the illumination-optical fiber 55 or the LD47, actuation control for stopping the LD47 completely, is carried out.

Then, explanation will be made as to distinct judgment between the degradation of the fluorescence luminescence component 3, and the breakage of the illumination-optical fiber 52 or the LD47. As mentioned above, after having detected the degradation of the fluorescence luminescence component 46, the LD47 is controlled so that the lighting of the LD47 may be done by the output by which the laser beam is not emanated from the LD47 without stopping it completely. At this state, when LD47 is being actuated even if the laser beam is not emitted, the user can judge that there is a degradation of the fluorescence luminescence component 46 occurs. On the other hand, when the drive of LD47 stops completely, the user can judge that there is a breakage of the illumination-optical fiber 52 or the LD47. Thus, also in the endoscope apparatus of the embodiment 4, in the LD-controlling-part 50''', the degradation of the fluorescence luminescence component 46 and the breakage of the illumination-optical fiber 52 or the LD47 can be detected distinctly.

Also in the endoscope apparatus of the embodiment 4, in the LD-controlling part 50''', the degradation of the fluorescence luminescence component 46 can be informed to the user by actuating control so as to output beeping, a warning sign, etc., after the degradation of the fluorescence luminescence component 46 is detected. Further, also in the endoscope apparatus of the embodiment 4, like the modified examples of the embodiment 1 shown in FIGS. 11-13, it can be constituted such that the optical adapter 60 may be attached and detached freely to the top part 39 of the insertion part 34. Effects in this case are almost the same as those of the example of modified embodiment shown in FIGS. 11-13.

In the embodiments 1-4 mentioned above, an endoscope apparatus for industrial use is shown as an example. However, it is not limited to the endoscope apparatus for industrial use, and it is applicable also to an endoscope apparatus of medical use.

The illumination light detecting optical system, and optical apparatus and endoscope apparatus provided with the same according to the present invention are useful for medical and industrial fields where observation is required while an observation object is being irradiated by using very thin and small sized hole of path.

What is claimed is:

1. An illumination light detecting optical system which is used for an optical apparatus comprising
   a light emitting element which emits excitation light;
   an insertion part of a long-narrow-shape;
   a fluorescence luminescence component arranged near a top of the insertion part;
   an excitation light guiding means which leads the excitation light emitted from the light emitting element to the fluorescence luminescence component; and
   a light detecting means which detects return light which is a part of the illumination light,
   wherein
   the illumination light detecting optical system comprises
   a first pillar-shaped transparent component for irradiating illumination light, which is arranged coaxially at a forward position of the fluorescence luminescence component;
   an illumination light-extracting means which extracts the illumination light out of the illumination light which is emanated from the fluorescence luminescence component to a forward direction, and enters into the inside of the first pillar-shaped transparent component, which enters at an angle smaller than a total reflection angle, into the side surface of the first pillar-shaped transparent component from the first pillar-shaped transparent component; and
   a deflecting means by which the extracted illumination light is directed toward the light detecting means.

2. The illumination light detecting optical system according to claim 1,
   wherein
   the total reflection angle is about 60°.

3. The illumination light detecting system according to claim 2,
   wherein
   the light detecting means consists of a transparent medium that has a refractive index smaller than that of the first pillar-shaped transparent component, and joining function, and a second pillar-shaped transparent component for extracting illumination light that has the same refractive index of the first pillar-shaped transparent component; and the side surface of the second pillar-shaped transparent component is joined through the transparent medium to the side surface of the first pillar-shaped transparent component.

4. The illumination light detecting system according to claim 1,
   wherein
   the light detecting means consists of a transparent medium that has a refractive index smaller than that of the first pillar-shaped transparent component and joining function, and a second pillar-shaped transparent component for extracting illumination light that has the same refractive index of the first pillar-shaped transparent component; and the side surface of the second pillar-shaped transparent component is joined through the transparent medium to the side surface of the first pillar-shaped transparent component.

5. The illumination light detecting system according to claim 4,
   wherein
   the transparent medium consists of adhesives and a ball lens.

6. The illumination light detecting system according to claim 5,
   wherein
   the deflecting means is constituted with a reflective surface consisting of a tilt surface formed at the top of the illumination light extracting component, and a reflective film arranged at the tilt surface.

7. An optical apparatus comprising
   the illuminating light detecting optical system according to claim 5;
   a light emitting element which emits excitation light;
   an insertion part of a long-narrow-shape;
   a fluorescence luminescence component arranged near the top of the insertion part;
   an excitation light guiding means which leads the excitation light emitted from the light emitting element to the fluorescence luminescence component;
   a light detecting means which detects return light which is a part of the illumination light; and
   a pillar-shaped transparent component for irradiating illumination light, which is arranged at a forward position of the fluorescence luminescence component.

8. The optical apparatus according to claim 7,
   wherein
   the light detecting means
   comprises
   a spectrum component which separates the light obtained through the illumination light detecting optical system into an excitation light component and a fluorescence component;
   light receiving elements which receive each of separated light;
   and
   an arithmetic apparatus for computing ratio of amounts of light received by each of the light receiving elements.

9. The optical apparatus according to claim 7, wherein the optical apparatus is an endoscope.

10. An endoscope apparatus
comprising
a light emitting element which emits light;
an insertion part inserted into an examination object space;
a fluorescence luminescence component arranged near a top of the insertion part;
a light detecting means which detects return light which is a part of the illumination light;
the illumination light detecting optical system according to claim 5;
wherein
the light detecting means
comprises
a light sensor;
a light guide for detecting light which is arranged so that one end may be faced to a rear end of the second pillar-shaped transparent component of the illumination light detecting optical system, and the other end may be faced to the optical sensor, wherein out of illumination light emanated from the fluorescence luminescence component toward a forward direction, light which is extracted through the second pillar-shaped transparent component of the illumination light extracting means, and deflected through the deflecting means is transmitted to the optical sensor;
a wavelength restricting component which is arranged between the other end of the light guide for detecting light, and the light sensor, wherein at least, the return light is transmitted, or reflected by restricting a predetermined wavelength of the illumination light, and the transmitted or reflected light is detected by the light sensor;
and
a controlling part which detects intensity of the light detected in the light sensor, and controls to detect degradation of the fluorescence luminescence component.

11. The illumination light detecting optical system according to claim 1,
wherein
the deflecting means is constituted with a reflective surface consisting of a tilt surface formed at the top of the illumination light extracting component, and a reflective film arranged at the tilt surface.

12. The illumination light detecting system according to claim 1,
wherein
the deflecting means is constituted with two reflective surface consisting of two tilt surfaces formed at the top of the illumination light extracting component, and two reflective films arranged at the two tilt surfaces.

13. An optical apparatus
comprising
the illuminating light detecting optical system according to claim 1;
a light emitting element which emits excitation light;
an insertion part of a long-narrow-shape;
a fluorescence luminescence component arranged near the top of the insertion part;
an excitation light guiding means which leads the excitation light emitted from the light emitting element to the fluorescence luminescence component;
and
a light detecting means which detects return light which is a part of the illumination light.

14. The optical apparatus according to claim 13,
wherein
the light detecting means comprises
a spectrum component which separates the light obtained through the illumination light detecting optical system into an excitation light component and a fluorescence component;
light receiving elements which receive each of separated light;
and
an arithmetic apparatus for computing ratio of amounts of light received by each of the light receiving elements.

15. The optical apparatus according to claim 13,
wherein
an light diffusing means is arranged at the top end surface of the first pillar-shaped transparent component.

16. The optical apparatus according to claim 15,
wherein
the light diffusion means is constituted such that a top end surface of the first pillar-shaped transparent component, and
an end surface side of a transparent component having the same refractive index as that of the first pillar-shaped transparent component are joined so that a ball lens array and adhesives which have different refractive index may be disposed between the surfaces.

17. The optical apparatus according to claim 15,
wherein
the light diffusion means is constituted such that a sand pattern is formed on, at least, one of the surfaces of a top end surface of the first pillar-shaped transparent component, and an end surface of a transparent component with the same refractive index as the first pillar-shaped transparent component, and further, these surfaces are joined so that adhesives having different refractive index may be disposed between the surfaces.

18. The optical apparatus according to claim 13, wherein the optical apparatus is an endoscope.

19. An endoscope apparatus
comprising
a light emitting element which emits light;
an insertion part inserted into an examination object space;
a fluorescence luminescence component arranged near a top of the insertion part;
a light detecting means which detects return light which is a part of the illumination light;
and
the illumination light detecting optical system according to claim 1;
wherein
the light detecting means
comprises
a light sensor;
a light guide for detecting light which is arranged so that one end may be faced to a rear end of the pillar-shaped transparent component of the illumination light extracting means, and the other end may be faced to the optical sensor, wherein out of illumination light emanated from the fluorescence luminescence component toward a forward direction, light which is extracted through the pillar-shaped transparent component of the illumination light extracting means, and deflected through the deflecting means is transmitted to the optical sensor;
a wavelength restricting component which is arranged between the other end of the light guide for detecting light, and the light sensor, wherein at least, the return light is transmitted, or reflected by restricting a predetermined wavelength of the illumination light, and the transmitted or reflected light is detected by the light sensor; and a controlling part which detects intensity of the light detected in the light sensor, and controls to detect degradation of the fluorescence luminescence component.

20. An illumination light detecting optical system, which is used for an optical apparatus, comprising a light emitting element for emitting excitation light;

an insertion part of a long-narrow-shape;

a fluorescence luminescence component arranged near the top of the insertion part;

an excitation light guiding means which leads the excitation light emitted from the light emitting element to the fluorescence luminescence component; and a light detecting means for detecting return light which is a part of the illuminating light;

and further comprising an illuminating light extracting means which consists of the pillar-shaped transparent component for extracting illumination light, and is arranged so that the light emanated from the very small part of the area, out of the illuminating light that is emanated from the fluorescence luminescence component toward forward direction, wherein a part of the area of an entrance surface overlaps with a very small part of the area of an exit surface of the fluorescence luminescence component, may be extracted through a part of the area of the entrance surface;

and a deflecting means by which the extracted illuminating light is directed toward the light detecting means.

21. The illumination light detecting system according to claim 20, wherein the deflecting means is constituted with two reflective surfaces consisting of two tilt surfaces formed at the top of the illumination light extracting component, and two reflective films arranged at the two tilt surfaces.

* * * * *